US012611184B2

(12) United States Patent
Guo et al.

(10) Patent No.: US 12,611,184 B2
(45) Date of Patent: Apr. 28, 2026

(54) ULTRASOUND IMAGING BY COMBINING COHERENT AND NON-COHERENT COMPOUNDING

(71) Applicant: SHENZHEN MINDRAY BIO-MEDICAL ELECTRONICS CO., LTD., Guangdong (CN)

(72) Inventors: Chongchong Guo, Shenzhen (CN); Jing Liu, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 27 days.

(21) Appl. No.: 18/498,916

(22) Filed: Oct. 31, 2023

(65) Prior Publication Data
US 2024/0138816 A1 May 2, 2024

(30) Foreign Application Priority Data
Oct. 31, 2022 (CN) .......................... 202211351307.7

(51) Int. Cl.
*A61B 8/00* (2006.01)

(52) U.S. Cl.
CPC .......... *A61B 8/5207* (2013.01); *A61B 8/5253* (2013.01); *A61B 2560/02* (2013.01)

(58) Field of Classification Search
CPC .......................... A61B 8/5253; G01S 15/8995
See application file for complete search history.

(56) References Cited

U.S. PATENT DOCUMENTS 10,571,554 B2 2/2020 Zhai et al.
11,521,335 B2 12/2022 Bjastad
(Continued)

FOREIGN PATENT DOCUMENTS

CN 108120988 A 6/2018
CN 112773392 A 5/2021
(Continued)

OTHER PUBLICATIONS

First Search dated Sep. 27, 2024, issued in related Chinese Patent Application No. 202211351307.7 (2 pages).

*Primary Examiner* — Nyrobi Celestine
(74) *Attorney, Agent, or Firm* — Sheppard Mullin Richter & Hampton LLP

(57) ABSTRACT

An ultrasound imaging method includes: transmitting ultrasound waves to a target tissue at at least two different transmission angles; obtaining an ultrasound echo signal corresponding to each transmission angle; for the ultrasound echo signal corresponding to each transmission angle, performing beamforming at at least two different receiving angles to obtain beamformed data; based on each transmission angle and the receiving angles corresponding to the beamformed data, performing at least one coherent compounding and at least one non-coherent compounding on the beamformed data to obtain compounded data, where each coherent compounding includes performing coherent compounding on beamformed data corresponding to a same receiving angle and different transmission angles to obtain a set of coherently compounded data corresponding to the same receiving angle, and each non-coherent compounding includes performing non-coherent compounding on at least two sets of coherently compounded data; and generating an ultrasound image based on the compounded data.

7 Claims, 10 Drawing Sheets

(56) References Cited

U.S. PATENT DOCUMENTS

| | | | | |
|---|---|---|---|---|
| 2003/0092989 | A1* | 5/2003 | Aichhorn | G01S 7/52085 |
| | | | | 600/443 |
| 2008/0208061 | A1* | 8/2008 | Halmann | G01S 15/8995 |
| | | | | 600/459 |
| 2013/0258805 | A1* | 10/2013 | Hansen | G01S 15/89 |
| | | | | 367/8 |
| 2022/0249064 | A1* | 8/2022 | Huang | A61B 8/54 |
| 2023/0099970 | A1* | 3/2023 | Luo | G01S 7/52063 |
| | | | | 600/443 |
| 2023/0277158 | A1* | 9/2023 | Call | G01S 15/8927 |
| | | | | 600/443 |

FOREIGN PATENT DOCUMENTS

| | | | |
|---|---|---|---|
| WO | 2022/082627 | A1 | 4/2022 |
| WO | 2024/167902 | A1 | 8/2024 |

* cited by examiner

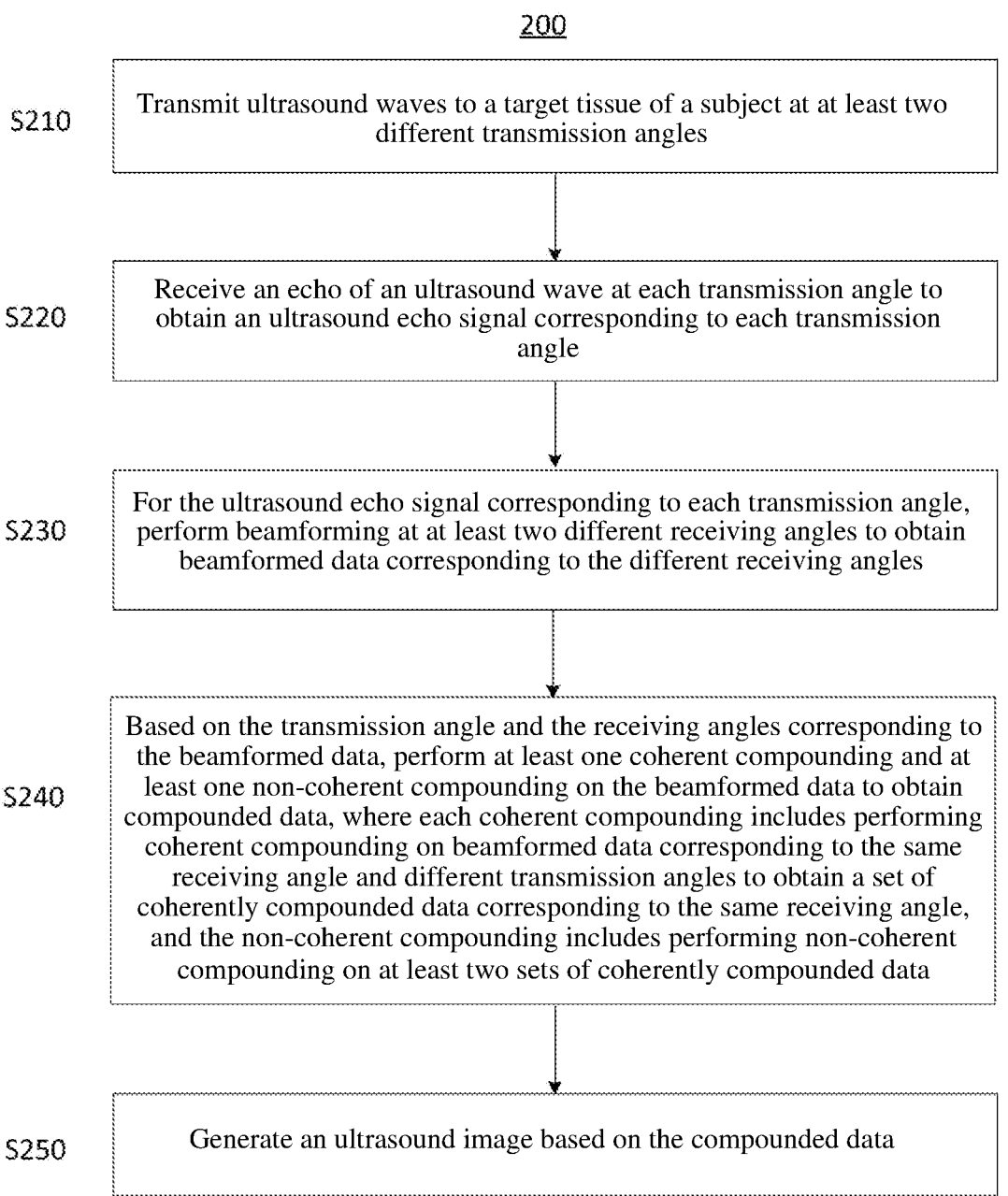

200

S210   Transmit ultrasound waves to a target tissue of a subject at at least two different transmission angles S220   Receive an echo of an ultrasound wave at each transmission angle to obtain an ultrasound echo signal corresponding to each transmission angle S230   For the ultrasound echo signal corresponding to each transmission angle, perform beamforming at at least two different receiving angles to obtain beamformed data corresponding to the different receiving angles S240   Based on the transmission angle and the receiving angles corresponding to the beamformed data, perform at least one coherent compounding and at least one non-coherent compounding on the beamformed data to obtain compounded data, where each coherent compounding includes performing coherent compounding on beamformed data corresponding to the same receiving angle and different transmission angles to obtain a set of coherently compounded data corresponding to the same receiving angle, and the non-coherent compounding includes performing non-coherent compounding on at least two sets of coherently compounded data S250   Generate an ultrasound image based on the compounded data

*FIG. 2*

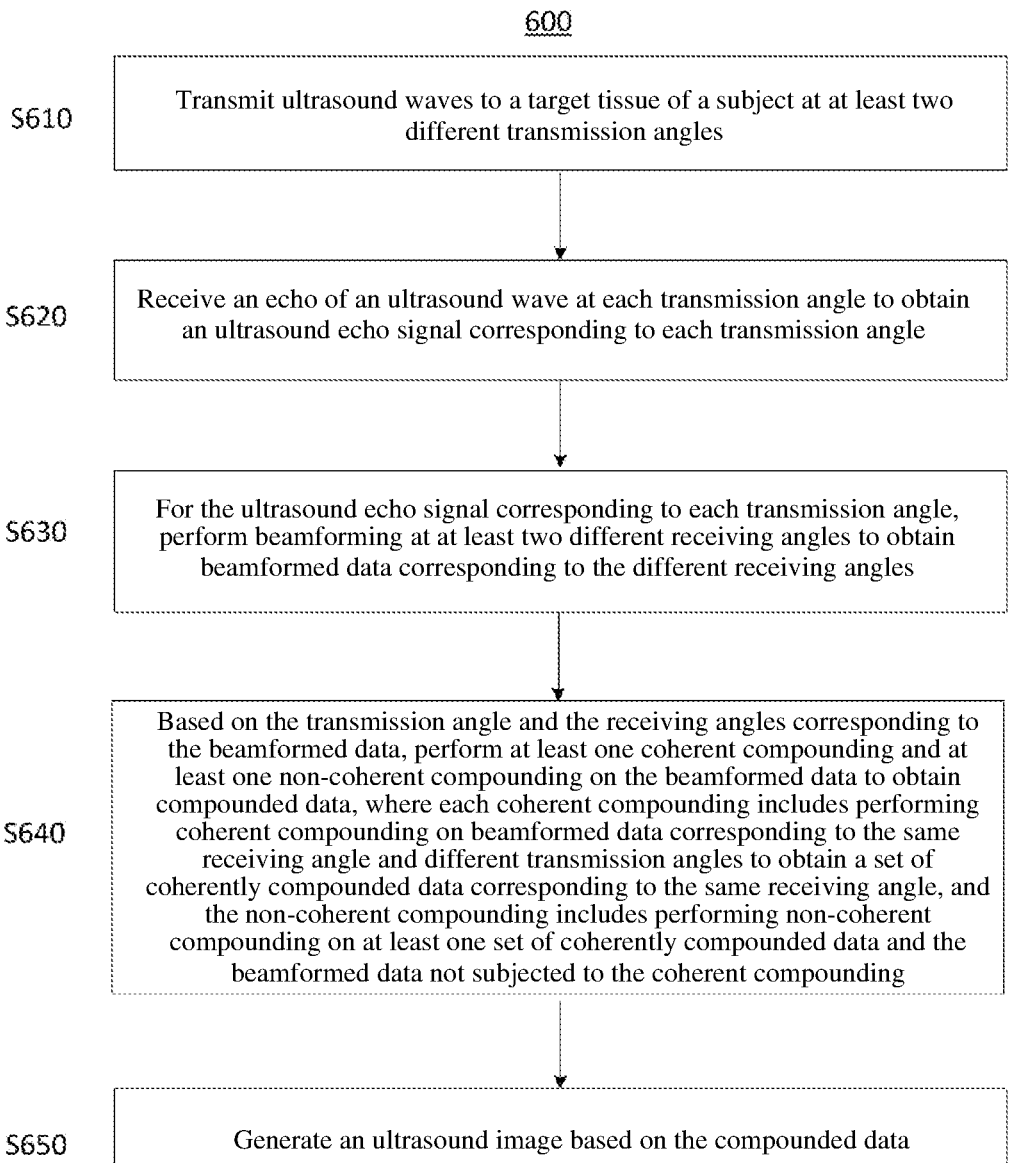

600

S610     Transmit ultrasound waves to a target tissue of a subject at at least two different transmission angles S620     Receive an echo of an ultrasound wave at each transmission angle to obtain an ultrasound echo signal corresponding to each transmission angle S630     For the ultrasound echo signal corresponding to each transmission angle, perform beamforming at at least two different receiving angles to obtain beamformed data corresponding to the different receiving angles S640     Based on the transmission angle and the receiving angles corresponding to the beamformed data, perform at least one coherent compounding and at least one non-coherent compounding on the beamformed data to obtain compounded data, where each coherent compounding includes performing coherent compounding on beamformed data corresponding to the same receiving angle and different transmission angles to obtain a set of coherently compounded data corresponding to the same receiving angle, and the non-coherent compounding includes performing non-coherent compounding on at least one set of coherently compounded data and the beamformed data not subjected to the coherent compounding S650     Generate an ultrasound image based on the compounded data

*FIG. 6*

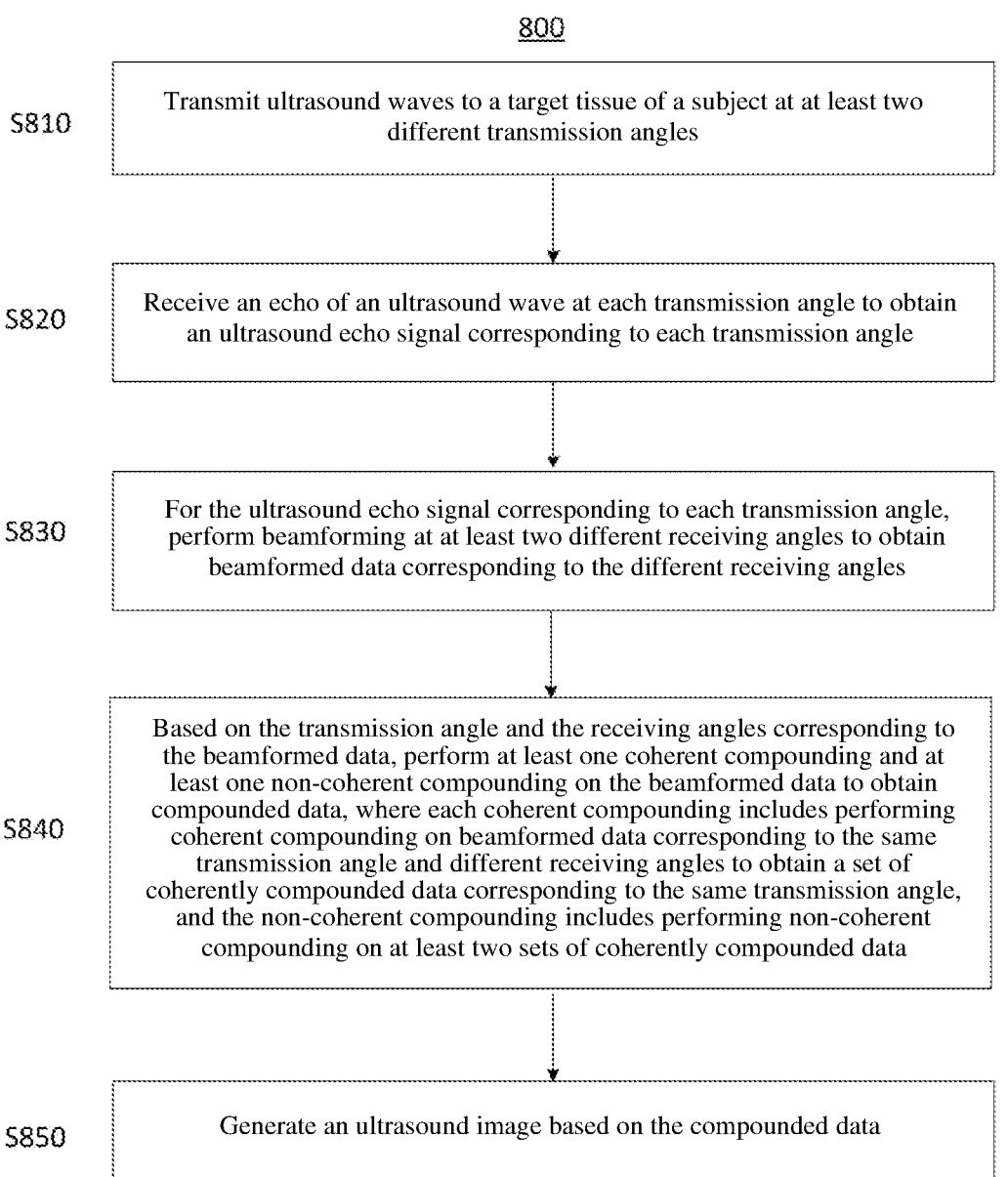

800

S810 — Transmit ultrasound waves to a target tissue of a subject at at least two different transmission angles S820 — Receive an echo of an ultrasound wave at each transmission angle to obtain an ultrasound echo signal corresponding to each transmission angle S830 — For the ultrasound echo signal corresponding to each transmission angle, perform beamforming at at least two different receiving angles to obtain beamformed data corresponding to the different receiving angles S840 — Based on the transmission angle and the receiving angles corresponding to the beamformed data, perform at least one coherent compounding and at least one non-coherent compounding on the beamformed data to obtain compounded data, where each coherent compounding includes performing coherent compounding on beamformed data corresponding to the same transmission angle and different receiving angles to obtain a set of coherently compounded data corresponding to the same transmission angle, and the non-coherent compounding includes performing non-coherent compounding on at least two sets of coherently compounded data S850 — Generate an ultrasound image based on the compounded data

*FIG. 8*

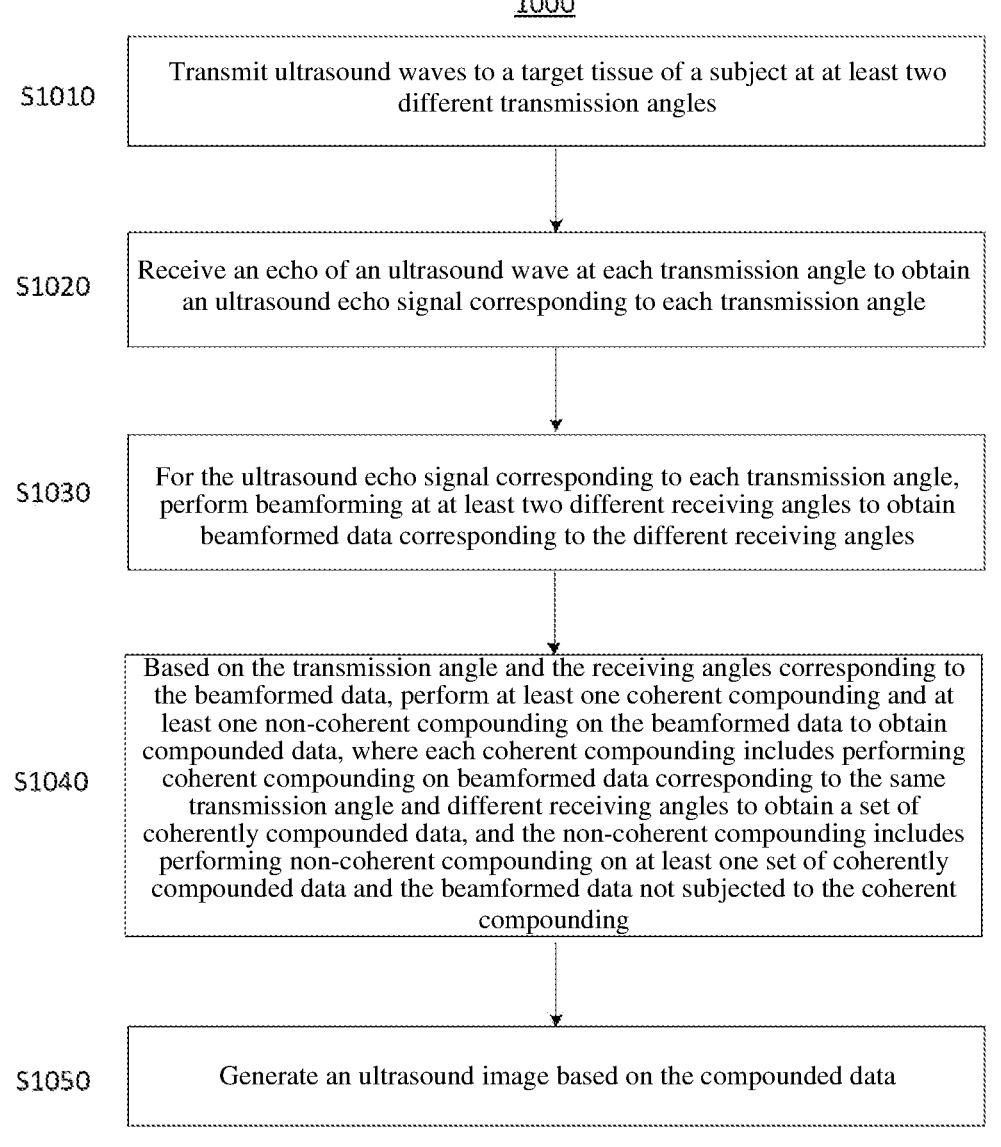

1000

S1010 — Transmit ultrasound waves to a target tissue of a subject at at least two different transmission angles S1020 — Receive an echo of an ultrasound wave at each transmission angle to obtain an ultrasound echo signal corresponding to each transmission angle S1030 — For the ultrasound echo signal corresponding to each transmission angle, perform beamforming at at least two different receiving angles to obtain beamformed data corresponding to the different receiving angles S1040 — Based on the transmission angle and the receiving angles corresponding to the beamformed data, perform at least one coherent compounding and at least one non-coherent compounding on the beamformed data to obtain compounded data, where each coherent compounding includes performing coherent compounding on beamformed data corresponding to the same transmission angle and different receiving angles to obtain a set of coherently compounded data, and the non-coherent compounding includes performing non-coherent compounding on at least one set of coherently compounded data and the beamformed data not subjected to the coherent compounding S1050 — Generate an ultrasound image based on the compounded data

*FIG. 10*

ULTRASOUND IMAGING BY COMBINING COHERENT AND NON-COHERENT COMPOUNDING

CROSS-REFERENCE TO RELATED APPLICATIONS

This application is based on and claims priority to and benefits of Chinese Patent Application No. 202211351307.7, filed on Oct. 31, 2022. The entire content of the above-referenced application is incorporated herein by reference.

TECHNICAL FIELD

The disclosure relates to the technical field of ultrasound imaging, and more specifically, to an ultrasound imaging method and an ultrasound imaging system.

BACKGROUND

Ultrasound imaging refers to the use of an ultrasound probe to transmit an ultrasound wave to a subject under examination or diagnosis, and then generate an ultrasound image based on an echo signal of the ultrasound wave. Ultrasound imaging has advantages such as real-time imaging, no radiation, wide audience, and low cost, and has been widely used in medical clinical diagnosis and routine physical examinations. The quality of an ultrasound image is crucial for clinical diagnosis.

By controlling different transmission delays based on information such as a depth and size of a region of interest, different transmission beam shapes can be formed, including focused waves, plane waves, and scattered waves based on a focal depth, as well as strong and weak focusing based on a focal zone, and vertical and deflected transmissions. Ultrasound waves at different transmission angles are reflected by a medium and received, and processed to form images corresponding to different angles, which are then spatially compounded to form a spatial compounded ultrasound image. The compounded image is formed by imaging with different acoustic wave shapes acting on the same medium and compounding resulting images. In spatial compounded ultrasound imaging, a tissue is imaged at various viewing angles. Images of different perspectives are generated at the viewing angles, and are then compounded to generate a compounded image. This can reduce speckle noise formed by ultrasound imaging, reduce a generated speckle variance, and increase the visibility of edges of the scatterer or boundaries of the tissue, thereby improving the image quality. However, a conventional spatial compounded imaging technology includes separately processing data received from angles to form views from different angles, instead of jointly processing data from a plurality of angles, thus affecting the spatial compounding effect.

SUMMARY

In the summary part, a series of concepts in simplified form are introduced, and will be further explained in detail in the part of description of the preferred embodiments. The summary of the disclosure does not mean trying to define key features and necessary technical features of the claimed technical solutions, let alone trying to determine the scope of protection of the claimed technical solutions.

A first aspect of an embodiment of the disclosure provides an ultrasound imaging method, the method including:

transmitting ultrasound waves to a target tissue of a subject at at least two different transmission angles;

receiving an echo of the ultrasound wave at each transmission angle to obtain an ultrasound echo signal corresponding to each transmission angle;

for the ultrasound echo signal corresponding to each transmission angle, performing beamforming at at least two different receiving angles to obtain beamformed data corresponding to the different receiving angles;

based on each transmission angle and the receiving angles corresponding to the beamformed data, performing at least one coherent compounding and at least one non-coherent compounding on the beamformed data to obtain compounded data, where each coherent compounding includes performing coherent compounding on beamformed data corresponding to a same receiving angle and different transmission angles to obtain a set of coherently compounded data corresponding to the same receiving angle, and each non-coherent compounding includes performing non-coherent compounding on at least two sets of coherently compounded data; and generating an ultrasound image based on the compounded data.

In some embodiments, performing coherent compounding on beamformed data corresponding to the same receiving angle and different transmission angles to obtain a set of coherently compounded data corresponding to a same receiving angle includes:

performing coherent compounding on the beamformed data corresponding to all transmission angles for each receiving angle to obtain coherently compounded data corresponding to said receiving angle; and performing non-coherent compounding on at least two sets of coherently compounded data includes: performing non-coherent compounding on the coherently compounded data corresponding to all receiving angles to obtain the compounded data.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles.

In some embodiments, the transmission angles include a first transmission angle, a second transmission angle, and a third transmission angle, the second transmission angle is the vertical transmission angle, and the first transmission angle and the third transmission angle are the deflected transmission angles that are symmetrical to each other with respect to the second transmission angle;

receiving angles corresponding to the first transmission angle include a first receiving angle and a second receiving angle, receiving angles corresponding to the second transmission angle include the first receiving angle, the second receiving angle, and a third receiving angle, receiving angles corresponding to the third transmission angle include the second receiving angle and the third receiving angle, the second receiving angle is the vertical receiving angle, and the first receiving angle and the third receiving angle are respectively parallel to the first transmission angle and the third transmission angle;

performing coherent compounding on the beamformed data corresponding to all transmission angles for each receiving angle to obtain coherently compounded data corresponding to said receiving angle includes:

performing coherent compounding on beamformed data corresponding to the first transmission angle and the first receiving angle and beamformed data corresponding to the second transmission angle and the first receiving angle, to obtain first coherently compounded data;

performing coherent compounding on beamformed data corresponding to the first transmission angle and the second receiving angle, beamformed data corresponding to the second transmission angle and the second receiving angle, and beamformed data corresponding to the third transmission angle and the second receiving angle, to obtain second coherently compounded data; and performing coherent compounding on beamformed data corresponding to the second transmission angle and the third receiving angle and beamformed data corresponding to the third transmission angle and the third receiving angle, to obtain third coherently compounded data; and performing non-coherent compounding on the coherently compounded data corresponding to all receiving angles to obtain the compounded data includes: performing non-coherent compounding on the first coherently compounded data, the second coherently compounded data, and the third coherently compounded data to obtain the compounded data.

In some embodiments, an included angle between a line along which each transmission angle is located and a line along which a corresponding receiving angle is located does not exceed a maximum included angle between a normal direction of an array element that transmits the ultrasound wave and said transmission angle.

In some embodiments, a number of different receiving angles among all receiving angles is same as that of different transmission angles among all transmission angles.

A second aspect of an embodiment of the disclosure provides an ultrasound imaging method, the method including:

transmitting ultrasound waves to a target tissue of a subject at at least two different transmission angles;

receiving an echo of an ultrasound wave at each transmission angle to obtain an ultrasound echo signal corresponding to each transmission angle;

for the ultrasound echo signal corresponding to each transmission angle, performing beamforming at at least two different receiving angles to obtain beamformed data corresponding to the different receiving angles;

based on each transmission angle and the receiving angles corresponding to the beamformed data, performing at least one coherent compounding and at least one non-coherent compounding on the beamformed data to obtain compounded data, where each coherent compounding includes performing coherent compounding on beamformed data corresponding to a same receiving angle and different transmission angles to obtain a set of coherently compounded data corresponding to the same receiving angle, and each non-coherent compounding includes performing non-coherent compounding on at least one set of coherently compounded data and the beamformed data not subjected to the coherent compounding; and generating an ultrasound image based on the compounded data.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles.

In some embodiments, performing coherent compounding on beamformed data corresponding to the same receiving angle and different transmission angles to obtain a set of coherently compounded data corresponding to the same receiving angle includes:

extracting, from beamformed data corresponding to the vertical receiving angle, beamformed data corresponding to the at least two deflected transmission angles that are symmetrical to each other with respect to the vertical transmission angle, and performing coherent compounding on the beamformed data corresponding to the at least two deflected transmission angles, to obtain the coherently compounded data; and wherein the data for the non-coherent compounding includes at least one set of coherently compounded data that corresponds to the vertical receiving angle, and the beamformed data not subjected to the coherent compounding that corresponds to the vertical receiving angle and the vertical transmission angle.

In some embodiments, performing coherent compounding on beamformed data corresponding to the same receiving angle and different transmission angles to obtain a set of coherently compounded data further includes:

performing coherent compounding on beamformed data corresponding to at least two different transmission angles corresponding to at least one of the deflected receiving angles to obtain coherently compounded data corresponding to said at least one deflected receiving angle; and wherein the data for the non-coherent compounding further includes the coherently compounded data corresponding to said at least one deflected receiving angle.

In some embodiments, the transmission angles include a first transmission angle, a second transmission angle, a third transmission angle, a fourth transmission angle, and a fifth transmission angle, the third transmission angle is the vertical transmission angle, the first transmission angle and the fifth transmission angle are the deflected transmission angles that are symmetrical to each other with respect to the third transmission angle, and the second transmission angle and the fourth transmission angle are the deflected transmission angles that are symmetrical to each other with respect to the third transmission angle;

receiving angles corresponding to the first transmission angle and the second transmission angle include a first receiving angle, a second receiving angle, and a third receiving angle, receiving angles corresponding to the third transmission angle include the first receiving angle, the second receiving angle, the third receiving angle, a fourth receiving angle, and a fifth receiving angle, receiving angles corresponding to the fourth transmission angle and the fifth transmission angle include the third receiving angle, the fourth receiving angle, and the fifth receiving angle, the third receiving angle is the vertical receiving angle, the first receiving angle and the fifth receiving angle are the deflected receiving angles that are symmetrical to each other with respect to the third receiving angle, and the second receiving angle and the fourth receiving angle are the deflected receiving angles that are symmetrical to each other with respect to the third receiving angle;

extracting, from beamformed data corresponding to the vertical receiving angle, beamformed data corresponding to the at least two deflected transmission angles that are symmetrical to each other with respect to the vertical transmission angle, and performing coherent compounding on the beamformed data corresponding to the at least two deflected transmission angles, to obtain the coherently compounded data include:

performing coherent compounding on beamformed data corresponding to the third receiving angle and the first transmission angle and beamformed data corresponding to the third receiving angle and the fifth transmission angle, to obtain fourth coherently compounded data; and performing coherent compounding on beamformed data corresponding to the third receiving angle and the second transmission angle and beamformed data corresponding to the third receiving angle and the fourth transmission angle, to obtain fifth coherently compounded data; and wherein the data for the non-coherent compounding includes the fourth coherently compounded data, the fifth coherently compounded data, and beamformed data corresponding to the third receiving angle and the third transmission angle.

A third aspect of an embodiment of the disclosure provides an ultrasound imaging method, the method including:

transmitting ultrasound waves to a target tissue of a subject at at least two different transmission angles;

receiving an echo of the ultrasound wave at each transmission angle to obtain an ultrasound echo signal corresponding to each transmission angle;

for the ultrasound echo signal corresponding to each transmission angle, performing beamforming at at least two different receiving angles to obtain beamformed data corresponding to the different receiving angles;

based on each transmission angle and the receiving angles corresponding to the beamformed data, performing at least one coherent compounding and at least one non-coherent compounding on the beamformed data to obtain compounded data, where each coherent compounding includes performing coherent compounding on beamformed data corresponding to the same transmission angle and different receiving angles to obtain a set of coherently compounded data corresponding to a same transmission angle, and each non-coherent compounding includes performing non-coherent compounding on at least two sets of coherently compounded data; and generating an ultrasound image based on the compounded data.

In some embodiments, performing coherent compounding on beamformed data corresponding to a same transmission angle and different receiving angles to obtain a set of coherently compounded data corresponding to the same transmission angle includes:

performing coherent compounding on the beamformed data corresponding to all receiving angles for each transmission angle to obtain coherently compounded data corresponding to said transmission angle; and performing non-coherent compounding on at least two sets of coherently compounded data includes: performing non-coherent compounding on the coherently compounded data corresponding to all transmission angles to obtain the compounded data.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles.

In some embodiments, the transmission angles include a first transmission angle, a second transmission angle, and a third transmission angle, the second transmission angle is the vertical transmission angle, the first transmission angle and the third transmission angle are the deflected transmission angles that are symmetrical to each other with respect to the second transmission angle;

receiving angles corresponding to the first transmission angle include a first receiving angle and a second receiving angle, receiving angles corresponding to the second transmission angle include the first receiving angle, the second receiving angle, and a third receiving angle, receiving angles corresponding to the third transmission angle include the second receiving angle and the third receiving angle, the second receiving angle is the vertical receiving angle, and the first receiving angle and the third receiving angle are respectively parallel to the first transmission angle and the third transmission angle;

performing coherent compounding on the beamformed data corresponding to all receiving angles for each transmission angle to obtain coherently compounded data corresponding to said transmission angle includes:

performing coherent compounding on beamformed data corresponding to the first transmission angle and the first receiving angle and beamformed data corresponding to the first transmission angle and the second receiving angle, to obtain sixth coherently compounded data;

performing coherent compounding on beamformed data corresponding to the second transmission angle and the first receiving angle, beamformed data corresponding to the second transmission angle and the second receiving angle, and beamformed data corresponding to the second transmission angle and the third receiving angle, to obtain seventh coherently compounded data; and performing coherent compounding on beamformed data corresponding to the third transmission angle and the second receiving angle and beamformed data corresponding to the third transmission angle and the third receiving angle, to obtain eighth coherently compounded data; and performing non-coherent compounding on the coherently compounded data corresponding to all transmission angles to obtain the compounded data includes:

performing non-coherent compounding on the sixth coherently compounded data, the seventh coherently compounded data, and the eighth coherently compounded data to obtain the compounded data.

In some embodiments, an included angle between a line along which each transmission angle is located and a line along which a corresponding receiving angle is located does not exceed a maximum included angle between a normal direction of an array element that transmits the ultrasound wave and said transmission angle.

In some embodiments, a number of different receiving angles among all the receiving angles is same as that of different transmission angles among all the transmission angles.

A fourth aspect of an embodiment of the disclosure provides an ultrasound imaging method, the method including:

transmitting ultrasound waves to a target tissue of a subject at at least two different transmission angles;

receiving an echo of an ultrasound wave at each transmission angle to obtain an ultrasound echo signal corresponding to each transmission angle;

for the ultrasound echo signal corresponding to each transmission angle, performing beamforming at at least two different receiving angles to obtain beamformed data corresponding to the different receiving angles;

based on each transmission angle and the receiving angles corresponding to the beamformed data, performing at least one coherent compounding and at least one non-coherent compounding on the beamformed data to obtain compounded data, where each coherent compounding includes performing coherent compounding on beamformed data corresponding to a same transmission angle and different receiving angles to obtain a set of coherently compounded data, and each non-coherent compounding includes performing non-coherent compounding on at least one set of coherently compounded data and beamformed data not subjected to the coherent compounding; and generating an ultrasound image based on the compounded data.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles parallel to the at least two deflected transmission angles.

In some embodiments, performing coherent compounding on beamformed data corresponding to the same transmission angle and different receiving angles to obtain a set of coherently compounded data includes:

extracting, from beamformed data corresponding to the vertical transmission angle, beamformed data corresponding to the at least two deflected receiving angles that are symmetrical to each other with respect to the vertical receiving angle, and performing coherent compounding on the beamformed data corresponding to the at least two deflected receiving angles, to obtain the coherently compounded data; and wherein the data for the non-coherent compounding includes at least one set of coherently compounded data that corresponds to the vertical transmission angle, and the beamformed data not subjected to the coherent compounding that corresponds to the vertical transmission angle and the vertical receiving angle.

In some embodiments, performing coherent compounding on beamformed data corresponding to the same transmission angle and different receiving angles to obtain a set of coherently compounded data further includes:

performing coherent compounding on beamformed data corresponding to at least two different receiving angles corresponding to at least one of the deflected transmission angles to obtain coherently compounded data corresponding to said at least one deflected transmission angle; and wherein the data for the non-coherent compounding further includes the coherently compounded data corresponding to said at least one deflected transmission angle.

In some embodiments, the transmission angles include a first transmission angle, a second transmission angle, a third transmission angle, a fourth transmission angle, and a fifth transmission angle, the third transmission angle is the vertical transmission angle, the first transmission angle and the fifth transmission angle are the deflected transmission angles that are symmetrical to each other with respect to the third transmission angle, and the second transmission angle and the fourth transmission angle are the deflected transmission angles that are symmetrical to each other with respect to the third transmission angle;

receiving angles corresponding to the first transmission angle and the second transmission angle include a first receiving angle, a second receiving angle, and a third receiving angle, receiving angles corresponding to the third transmission angle include the first receiving angle, the second receiving angle, the third receiving angle, a fourth receiving angle, and a fifth receiving angle, receiving angles corresponding to the fourth transmission angle and the fifth transmission angle include the third receiving angle, the fourth receiving angle, and the fifth receiving angle, the third receiving angle is the vertical receiving angle, the first receiving angle and the fifth receiving angle are the deflected receiving angles that are symmetrical to each other with respect to the third receiving angle, and the second receiving angle and the fourth receiving angle are the deflected receiving angles that are symmetrical to each other with respect to the third receiving angle;

extracting, from beamformed data corresponding to the vertical transmission angle, beamformed data corresponding to the at least two deflected receiving angles that are symmetrical to each other with respect to the vertical receiving angle, and performing coherent compounding on the beamformed data corresponding to the at least two deflected receiving angles, to obtain the coherently compounded data include:

performing coherent compounding on beamformed data corresponding to the third transmission angle and the first receiving angle and beamformed data corresponding to the third transmission angle and the fifth receiving angle, to obtain ninth coherently compounded data; and performing coherent compounding on beamformed data corresponding to the third transmission angle and the second receiving angle and beamformed data corresponding to the third transmission angle and the fourth receiving angle, to obtain tenth coherently compounded data; and wherein the data for the non-coherent compounding includes the ninth coherently compounded data, the tenth coherently compounded data, and beamformed data corresponding to the third transmission angle and the third receiving angle.

A fifth aspect of an embodiment of the disclosure provides an ultrasound imaging system, including:

an ultrasound probe;

a transmitter circuit configured to excite the ultrasound probe to transmit an ultrasound wave to a target tissue;

a receiver circuit configured to control the ultrasound probe to receive an ultrasound echo signal of the ultrasound wave;

a processor configured to perform the ultrasound imaging method as described above, to generate an ultrasound image; and a display configured to display the ultrasound image.

According to the ultrasound imaging method and the ultrasound imaging system in the embodiments of the disclosure, both coherent compounding and non-coherent compounding are performed on beamformed data corresponding to different transmission angles or different receiving angles, and amplitude information and phase information of data corresponding to different angles can be combined, thereby improving the image quality of an ultrasound image.

BRIEF DESCRIPTION OF THE DRAWINGS

The above and other objects, features and advantages of the disclosure will become more apparent from the description of embodiments of the disclosure in detail with reference to the accompanying drawings. The accompanying drawings, which are intended to provide a further understanding of embodiments of the disclosure and constitute a part of this specification, are intended to explain the disclosure together with the embodiments of the disclosure and not to limit the disclosure. In the accompanying drawings, like reference numerals generally indicate like components or steps.

FIG. 2 is a schematic flowchart of an ultrasound imaging method according to an embodiment of the disclosure;

FIG. 6 is a schematic diagram of an ultrasound imaging method according to another embodiment of the disclosure;

FIG. 8 is a schematic diagram of an ultrasound imaging method according to another embodiment of the disclosure;

FIG. 10 is a schematic diagram of an ultrasound imaging method according to another embodiment of the disclosure.

DESCRIPTION OF THE PREFERRED EMBODIMENTS

In order to make the objects, technical solutions, and advantages of the disclosure more apparent, the example embodiments according to the disclosure will be described in detail below with reference to the accompanying drawings. Apparently, the embodiments described are merely some, rather than all, of the embodiments of the disclosure. It should be understood that the disclosure is not limited by the example embodiments described herein. All other embodiments derived by those skilled in the art without creative efforts on the basis of the embodiments of the disclosure described in the disclosure shall fall within the scope of protection of the disclosure.

In the following description, a large number of specific details are given to provide a more thorough understanding of the disclosure. However, it is obvious to those skilled in the art that the disclosure can be implemented without one or more of these details. In other examples, some well-known technical features in the art are not described in order to avoid obscuring the disclosure.

It should be understood that, the disclosure can be implemented in different forms and should not be construed as being limited to the embodiments presented herein. On the contrary, these embodiments are provided to make the disclosure thorough and complete, and to fully convey the scope of the disclosure to those skilled in the art.

The terms used herein are intended only to describe specific embodiments and do not constitute a limitation to the disclosure. As used herein, the singular forms of "a", "an", and "the/this" are also intended to include plural forms, unless the context clearly indicates otherwise. It should also be appreciated that the terms "composed of" and/or "including", when used in the description, determine the existence of described features, integers, steps, operations, elements, and/or components, but do not exclude the existence or addition of one or more other features, integers, steps, operations, elements, components, and/or groups thereof. As used herein, the term "and/or" includes any and all combinations of relevant listed items.

For a thorough understanding of the disclosure, a detailed structure will be proposed in the following description to explain the technical solutions proposed in the disclosure. The optional embodiments of the disclosure are described in detail as follows. However, the disclosure may also have other implementations in addition to these detailed descriptions.

Figure 1:
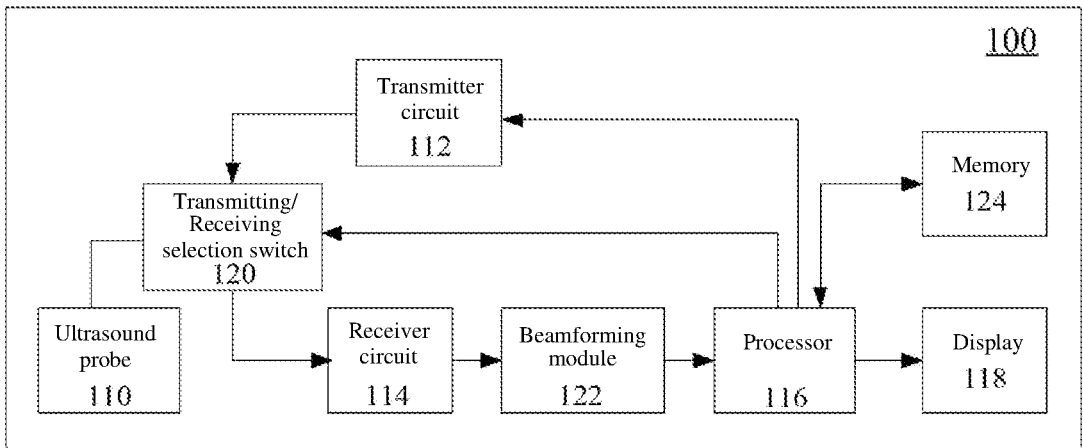
FIG. 1 is a block diagram of a structure of an ultrasound imaging system according to an embodiment of the disclosure.

In the following, first, an ultrasound imaging system according to an embodiment of the disclosure is described with reference to FIG. 1. FIG. 1 is a block diagram of a schematic structure of an ultrasound imaging system 100 according to an embodiment of the disclosure.

As shown in FIG. 1, the ultrasound imaging system 100 includes an ultrasound probe 110, a transmitter circuit 112, a receiver circuit 114, a processor 116, and a display 118. Further, the ultrasound imaging system may further include a transmitting/receiving selection switch 120 and a beamforming module 122, and the transmitter circuit 112 and the receiver circuit 114 may be connected to the ultrasound probe 110 through the transmitting/receiving selection switch 120.

The ultrasound probe 110 includes a plurality of transducer array elements. The plurality of transducer array elements may be arranged into a row to form a linear array, or arranged into a two-dimensional matrix to form an area array. Alternatively, the plurality of transducer array elements may form a convex array. The transducer array element is configured to transmit an ultrasound wave based on an excitation electrical signal, or convert a received ultrasound wave into an electrical signal. Therefore, each transducer array element may be configured to implement mutual conversion of an electrical pulse signal and an ultrasound wave, so as to transmit an ultrasound wave to a tissue in a target region of a subject, or may be configured to receive an echo of the ultrasound wave that is reflected by the tissue.

During ultrasound imaging, a transmitting sequence and a receiving sequence may be used to control which transducer array elements are used to transmit an ultrasound wave and which transducer array elements are used to receive an ultrasound wave, or control the transducer array elements to be used to transmit an ultrasound wave or receive an echo of the ultrasound wave in different slots. The transducer array elements participating in transmission of the ultrasound wave can be simultaneously excited by the electrical signal, so as to simultaneously transmit the ultrasound wave; or the transducer array elements participating in transmission of the ultrasound wave may be excited by several electrical signals having a specific time interval, so as to continuously transmit ultrasound waves having a specific time interval.

In an ultrasound imaging process, the transmitter circuit 112 generates a transmitting sequence under control of the processor 116. The transmitting sequence is used to control some or all of the plurality of transducer array elements to transmit an ultrasound wave to a target tissue. Parameters of the transmitting sequence include positions of the transmitting transducer array elements, the number of the transducer array elements, and transmission parameters of an ultrasound beam, such as amplitude, frequency, times of transmissions, transmission interval, transmission angle, waveform, and focusing position. In some cases, the transmitter circuit 112 is further configured to delay a phase of a transmitted beam, such that different transducer array elements transmit ultrasound waves at different moments, and ultrasound beams transmitted can be focused in a predetermined region of interest. Parameters of the transmitting sequence corresponding to different imaging modes may be different. After an ultrasound echo signal is received by the receiver circuit 114 and processed by a subsequent module and corresponding algorithm, ultrasound images of different imaging modes may be generated.

The receiver circuit 114 may include one or more amplifiers, analog-to-digital converters, and the like. The amplifier is configured to amplify the received ultrasound echo signal after proper gain compensation. The analog-to-digital converter is configured to sample an analog echo signal at predetermined time intervals, so as to convert same into a digitalized signal. The digitalized echo signal still retains amplitude information, frequency information, and phase information. The receiver circuit 114 sends the ultrasound echo signal to the beamforming module 122 for processing.

The beamforming module 122 performs processing such as focusing delaying, weighting, and channel summation on the ultrasound echo signals, and then sends the ultrasound echo signals to the processor 116. The processor 116 performs signal detection, signal enhancement, data conversion, logarithmic compression, and other processing on the ultrasound echo signals to form an ultrasound image. The ultrasound image obtained by the processor 116 may be displayed on the display 118 or stored in a memory 124.

Optionally, the processor 116 may be implemented by software, hardware, firmware, or any combination thereof, and may use one or more application specific integrated circuits (ASICs), one or more universal integrated circuits, one or more microprocessors, one or more programmable logic devices, or a combination of the above circuits or devices, or other suitable circuits or devices. Moreover, the processor 116 can control other components in the ultrasound imaging system 100 to perform corresponding steps of the methods in the various embodiments in this specification.

The display 118 is connected to the processor 116, and the display 118 may be a touchscreen display, a liquid crystal display, or the like; or the display 118 may be an independent display such as a liquid crystal display or a television independent of the ultrasound imaging system 100; or the display 118 may be a display of an electronic device such as a smartphone or a tablet computer. There may be one or more displays 118.

The display 118 may display the ultrasound image obtained by the processor 116. In addition, the display 118 may further provide a user with a graphical interface to perform human-machine interaction while displaying an ultrasound image, set one or more controlled objects on the graphical interface, and provide the user with a human-machine interaction apparatus to input operation instructions to control these controlled objects, so as to perform corresponding control operations. For example, an icon is displayed on the graphical interface, and the human-machine interaction apparatus may be used to operate the icon to perform a specific function, for example, drawing a box of a region of interest on the ultrasound image.

Optionally, the ultrasound imaging system 100 may alternatively include another human-machine interaction apparatus other than the display 118 that is connected to the processor 116. For example, the processor 116 may be connected to the human-machine interaction apparatus through an external input/output port, and the external input/output port may be a wireless communications module, or a wired communications module, or a combination of both. The external input/output port may be alternatively implemented based on a USB, a bus protocol such as CAN, and/or a wired network protocol.

The human-machine interaction apparatus may include an input device configured to detect input information of a user. The input information may be, for example, a control instruction for a time sequence of transmitting/receiving ultrasound waves, or an operation input instruction of drawing a point, a line, or a box on the ultrasound image or the like, or may include another type of instruction. The input device may include one or a combination of a keyboard, a mouse, a rolling wheel, a trackball, a mobile input device (such as a mobile device with a touchscreen display or a mobile phone), a multi-function knob, and the like. The human-machine interaction apparatus may further include an output device such as a printer.

The ultrasound imaging system 100 may further include a memory 124 for storing instructions executed by the processor, received ultrasound echoes, ultrasound images, and the like. The memory may be a flash memory card, a solid state memory, a hard disk, or the like. The memory may be a volatile memory and/or a non-volatile memory, a removable memory and/or a non-removable memory, or the like.

It should be understood that the components included in the ultrasound imaging system 100 shown in FIG. 1 are only schematic, and more or fewer components may be included. This is not limited in the disclosure.

In the following, an ultrasound imaging method according to an embodiment of the disclosure is described with reference to FIG. 2. FIG. 2 is a schematic flowchart of an ultrasound imaging method 200 according to an embodiment of the disclosure.

As shown in FIG. 2, the ultrasound imaging method 200 according to an embodiment of the disclosure includes the following steps.

In step S210, ultrasound waves are transmitted to a target tissue of a subject at at least two different transmission angles.

In step S220, an echo of the ultrasound wave is received at each transmission angle to obtain an ultrasound echo signal corresponding to each transmission angle.

In step S230, for the ultrasound echo signal corresponding to each transmission angle, beamforming is performed at at least two different receiving angles to obtain beamformed data corresponding to the different receiving angles.

In step S240, based on each transmission angle and the receiving angles corresponding to the beamformed data, at least one coherent compounding and at least one non-coherent compounding are performed on the beamformed data to obtain compounded data, where each coherent compounding includes performing coherent compounding on beamformed data corresponding to a same receiving angle and different transmission angles to obtain a set of coherently compounded data corresponding to the same receiving angle, and each non-coherent compounding includes performing non-coherent compounding on at least two sets of coherently compounded data.

In step S250, an ultrasound image is generated based on the compounded data.

Embodiments of the disclosure relate to an ultrasound spatial compounding technology. Spatial compounding can reduce speckle noise formed by ultrasound imaging, reduce a generated speckle variance, and increase the visibility of edges of the scatterer or boundaries of the tissue, thereby improving the image quality. The speckle noise is speckles produced through coherent superposition of scattered echoes of a homogeneous tissue, and is not noise in essence. However, because the homogeneous tissue should ideally have a smooth image, these speckles become noise that affects the image effect. If a relative position of an ultrasound probe and a tissue is fixed, a position of a speckle is fixed, but if the relative position of the ultrasound probe and the tissue is changed, a position of a speckle image also changes. Based on the above principles, the spatial compounding technology keeps the relative position of the ultrasound probe and the tissue unchanged, but a direction of a transmission angle or a receiving angle of an acoustic beam changes, which is equivalent to the position of the ultrasound probe and the tissue being changed, thus obtaining completely different speckle images. After spatial alignment, speckle noise at different angles no longer corresponds to the same pixel, and therefore, a smooth effect can be achieved after image superposition.

Moreover, spatial compounding may also produce a better display effect on strongly reflective interfaces with different angles of inclination. When ultrasound is incident on the strongly reflective interfaces in a tissue, it will produce a strong reflection, so that only when an incident direction is perpendicular to a reflective interface, an ultrasound echo signal can return to the ultrasound probe. Scanning at different deflection angles can make it possible to detect interfaces in different directions; and when an interface of the tissue is a curved surface, since different parts of the curved surface are imaged at different deflection angles, the continuity of the curved surface can be improved after spatial compounding.

The ultrasound imaging method of this embodiment of the disclosure can be used for grayscale imaging, or may be applied to a Doppler imaging mode and other imaging modes; or spatially, the method may be applied to conventional two-dimensional ultrasound imaging, or may be applied to three-dimensional ultrasound imaging or four-dimensional ultrasound imaging.

Specifically, in step S210, the ultrasound probe is controlled to transmit ultrasound waves at different transmission angles in sequence. The ultrasound probe may be any type of ultrasound probe such as a linear array probe, a convex array probe, a planar array probe, or a phased array probe. The ultrasound waves transmitted by the ultrasound probe may be focused ultrasound waves or non-focused ultrasound waves. Different transmission angles are achieved through different transmission delays, while the relative position of the ultrasound probe and the tissue remains unchanged. In an embodiment, the ultrasound probe performs one vertical transmission and at least one deflected transmission.

Exemplarily, if the transmitted ultrasound waves are focused ultrasound waves, a plurality of transducer array elements of the ultrasound probe are controlled to focus ultrasound beams in a target position, such that a better image resolution and contrast can be obtained in the target position; and a process of guiding sound fields of different transducer array elements to superpose in the target position is a transmission and focusing process. Specifically, a transmitting pulse generated by a transmitter circuit excites various transducer array elements according to a specific delay time, so that a transducer array element farther away from a focusing position performs transmission earlier, and the correspondingly set delay time is shorter; and transducers that are closer to the focusing position are transmitted later, and the correspondingly set delay time is longer. In this way, ultrasound waves transmitted by all transducer array elements may reach a target position at the same time, and form a focus in the target position. For focused ultrasound waves, focusing positions corresponding to different transmission angles are different.

Unfocused ultrasound waves mainly include plane waves and scattered waves. For plane waves, the transducer array elements in the ultrasound probe may be controlled to excite synchronously to generate ultrasound waves parallel to a plane of the transducer array elements; alternatively, the transducer array elements are excited in sequence based on a delay time calculated based on a deflection angle, to transmit ultrasound waves at a specific deflection angle. Divergent waves mean that there are one or more virtual focus points behind the ultrasound probe, and transmitting waveforms take the virtual focus points as centers. Before a transmission delay is set to obtain an arc-shaped transmitting wave, as a depth increases, the divergent waves gradually diverge for a larger field of view with a smaller aperture.

In step S220, the echo of the ultrasound wave is received at each transmission angle to obtain the ultrasound echo signal corresponding to each transmission angle. Exemplarily, each time a transmission is completed, a receiver circuit controls the transducer array elements in the ultrasound probe to receive echoes of the ultrasound waves transmitted in the previous step from each receiving point in a target region, and convert the echoes into electrical signals to obtain ultrasound echo signals. Because different receiving points in the tissue have different distances from the same transducer array element, and distances from the same receiving point to different transducer array elements are also different, a transducer array element may receive ultrasound echo signals with signal strength variations over a period of time, and convert the ultrasound echo signals into electrical signals which then become an analog signal with continuously changing amplitude. The analog signal is referred to as a channel signal corresponding to this transmission.

Exemplarily, after converting the received ultrasound waves into electrical signals, the transducer array element may further perform gain amplification, filtering, analog-to-digital conversion, and the like on the electrical signals, which are then sent to a beamforming module for beamforming. When an ultrasound wave is propagated in the tissue, its intensity decreases with an increase of a propagation distance. Therefore, it is required to perform gain amplification on an ultrasound echo signal, that is, a gain change of an amplifier is controlled, such that magnification of an ultrasound echo signal with a longer propagation distance is relatively large, and magnification of an ultrasound echo signal with a shorter propagation distance is relatively small, to compensate for attenuation of ultrasound waves at different depths. At the same time, a noise signal in the ultrasound echo signal is also amplified, and because the noise does not have attenuation characteristics of the ultrasound signal, and after the gain amplification, the noise increases with an increase of different distances, it is further required to filter the ultrasound echo signal after the gain amplification. The analog-to-digital conversion refers to conversion of an analog signal into a digital signal for subsequent digital signal processing.

In step S230, for the ultrasound echo signal corresponding to each transmission angle, beamforming is performed at the at least two different receiving angles to obtain the beamformed data corresponding to the different receiving angles. The beamforming refers to performing corresponding processing such as delaying and weighted summation on different channel signals in the ultrasound echo signal corresponding to each transmission angle, which is a transformation process from channel domain data to imaging receiving grid points. Due to different distances from the same receiving point in the tissue to different transducer array elements, channel data at the same receiving point that is output by different transducer array elements have delay differences, and a function of delaying processing is to perform phase alignment on different channel signals. Then, weighted summation is performed on different channel data at the same receiving point, to obtain a beamformed ultrasound echo signal.

When beamforming is performed, an angle formed by a line between a receiving grid point and a center point of a receiving aperture used for receiving beamforming and a normal line is referred to as a receiving angle. Performing beamforming at different receiving angles means that in each beamforming process, delays are respectively calculated based on different receiving angles, to obtain beamformed data corresponding to the different receiving angles. Performing beamforming at different receiving angles can achieve, through an algorithm, an effect similar to a plurality of deflected transmissions.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles. When receiving angles or transmission angles are symmetrical based on the vertical transmission angle, obtained ultrasound echo signals have higher coherence, and the effect of coherent compounding is better. Moreover, when the number of transmission angles and the number of receiving angles are the same, it is easier to perform subsequent data processing.

Figure 3:
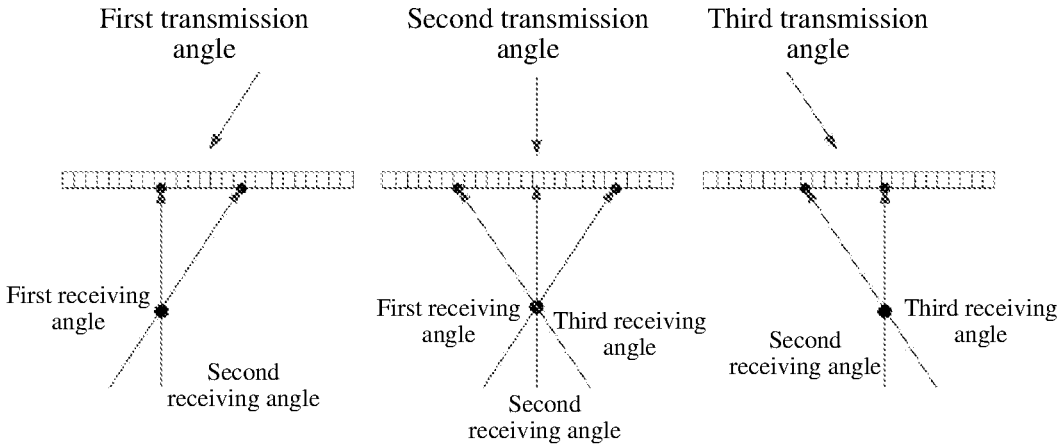
FIG. 3 is a schematic diagram of one transmission angle corresponding to a plurality of receiving angles according to an embodiment of the disclosure.

In a conventional ultrasound imaging process, one transmission angle corresponds to only one receiving angle, but in the embodiment of the disclosure, one transmission angle not only corresponds to one receiving angle, but may correspond to two or more receiving angles. For example, as shown in FIG. 3, when transmission is performed at a first transmission angle, the receiving angle includes a first receiving angle and a second receiving angle; when transmission is performed at a second transmission angle, the receiving angle includes the first receiving angle, a second receiving angle, and a third receiving angle; and when transmission is performed at a third transmission angle, the receiving angle includes the second receiving angle and the third receiving angle. That is, although transmission is performed three times at different transmission angles, beamforming processing is performed seven times in total, and seven frames of different beamformed data are obtained. If beamforming processing is separately performed at three different receiving angles when transmission is performed at the first receiving angle and the third receiving angle, nine frames of different beamformed data may be obtained by performing transmission three times, so that richer data is obtained at unchanged transmission angles.

In the example of FIG. 3, the second transmission angle is the vertical transmission angle, and the first transmission angle and the third transmission angle are the deflected transmission angles that are symmetrical to each other with respect to the second transmission angle. The second receiving angle is the vertical receiving angle, and the first receiving angle and the third receiving angle are respectively parallel to the first transmission angle and the third transmission angle. Therefore, it may be ensured that each transmission angle has a receiving angle parallel to the transmission angle and at least one deflected receiving angle to ensure the imaging effect.

The number of transmission angles and the number of receiving angles in the embodiment of the disclosure may be set according to actual needs. For example, when a relatively low frame rate of an ultrasound image is required, more transmission angles or receiving angles may be used to improve the quality of the ultrasound image; and when a relatively high frame rate of an ultrasound image is required, a number of transmission angles or receiving angles may be appropriately reduced to increase the frame rate.

Figure 4:
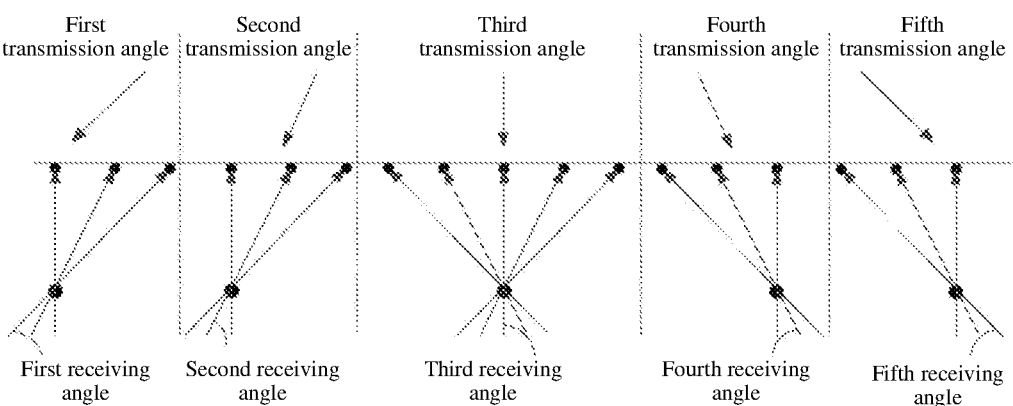
FIG. 4 is a schematic diagram of one transmission angle corresponding to a plurality of receiving angles according to another embodiment of the disclosure.

In general, the transmission angle and the receiving angle are the same. To prevent excessive deflection between the transmission angle and the receiving angle from reducing signal strength and a signal-to-noise ratio, when multi-angle receiving is performed in the embodiment of the disclosure, an included angle between a line along which each transmission angle is located and a line along which a corresponding receiving angle is located does not exceed a maximum included angle between a normal direction of an array element that transmits the ultrasound wave and the transmission angle. As shown in FIG. 4, when ultrasound waves are transmitted at five different transmission angles, beamforming processing is performed on ultrasound echo data corresponding to each transmission angle three to five times, and a total of seventeen frames of beamformed data are obtained. The maximum included angle between the normal direction of the array element and the transmission angle is an included angle between a normal line of the array element and each of the first transmission angle and a fifth transmission angle, and the included angle between the line along which each transmission angle is located and the line along which the corresponding receiving angle is located does not exceed the included angle. Based on this principle, receiving angles corresponding to the first transmission angle are the first receiving angle, the second receiving angle, and the third receiving angle. Because an included angle between a line along which the first transmission angle is located and each of a line along which the fourth receiving angle is located and a line along which the fifth receiving angle is located exceeds the included angle between the first transmission angle and the normal line of the array element, when transmission is performed at the first transmission angle, receiving is no longer performed at the fourth receiving angle and the fifth receiving angle. However, in other embodiments, for each transmission angle, receiving may be performed at five receiving angles to obtain more tissue information.

After step S230 is performed, beamformed data corresponding to a plurality of angles is obtained, and beamformed data corresponding to each angle corresponds to one transmission angle and one receiving angle. The beamformed data corresponding to each angle can form one view, and different beamformed data correspond to different transmission angles and/or receiving angles. Then, spatial compounding is performed on the different beamformed data to obtain compounded data used to form a frame of ultrasound image. Because a signal with both amplitude and phase modulated is obtained after the beamforming is completed, envelope detection and logarithmic compression also need to be performed to further obtain amplitude information of an echo for imaging. An object of the envelope detection is to extract amplitude information from a radio frequency signal. Exemplarily, a Hilbert transform method may be used for envelope detection. An original signal is subjected to the Hilbert transform to obtain an orthogonal signal of the original signal. With the original signal as a real part, and the orthogonal signal obtained by the Hilbert transform as an imaginary part, a complex analytic signal is constructed. A modulus of the signal is an envelope of the original signal. An ultrasound echo signal after the envelope detection is an amplitude envelope curve of the ultrasound echo signal. Values on the envelope curve cannot be directly used for imaging, and an original value range of the envelope curve needs to be mapped to an imaging interval of the ultrasound imaging system, that is, logarithmic compression. After the envelope detection and logarithmic compression, a real signal is transformed into a complex signal.

In step S240, the spatial compounding is performed on the beamformed data corresponding to the different transmission angles or the different receiving angles. If the beamformed data is compounded before the envelope detection, the beamformed data carries phase information, and the phase information of the data is used during the compounding. Such compounding is referred to as coherent compounding. If the beamformed data is compounded after the envelope detection, data used for compounding does not carry phase information, but amplitude information of the data is used during compounding. Such compounding is referred to as non-coherent compounding. According to this embodiment of the disclosure, both the coherent compounding and the non-coherent compounding are performed, and at the same time, amplitude information and phase information of data corresponding to different angles are used to improve the image quality.

The coherent compounding is to perform the coherent compounding on the beamformed data corresponding to the same receiving angle and different transmission angles for phase alignment. During the non-coherent compounding, because the data does not carry phase information, the non-coherent compounding may be performed on the coherently compounded data corresponding to the different receiving angles. The coherent compounding is performed on the beamformed data corresponding to the same receiving angle and the different transmission angles, and sound field information of different transmission angles is coherently compounded at the same receiving angle, which improves the image signal-to-noise ratio and spatial resolution. The coherent compounding can also weaken the impact of a plurality of reflections at boundaries of strong echoes, which is beneficial to noise reduction in a lumen of a blood vessel. The non-coherent compounding is performed on the coherently compounded data corresponding to the different receiving angles, such that speckle noise is suppressed, noise of an ultrasound image is reduced, and the image quality is further improved. Moreover, the coherent compounding of data at the same receiving angle may be performed based on the receiving aperture, which reduces the complexity of data processing.

In some embodiments, the coherent compounding includes performing coherent compounding on the beamformed data corresponding to all the transmission angles for each receiving angle to obtain coherently compounded data corresponding to the receiving angle; and the non-coherent compounding includes performing non-coherent compounding on the coherently compounded data corresponding to all receiving angles to obtain the compounded data.

Figure 5:
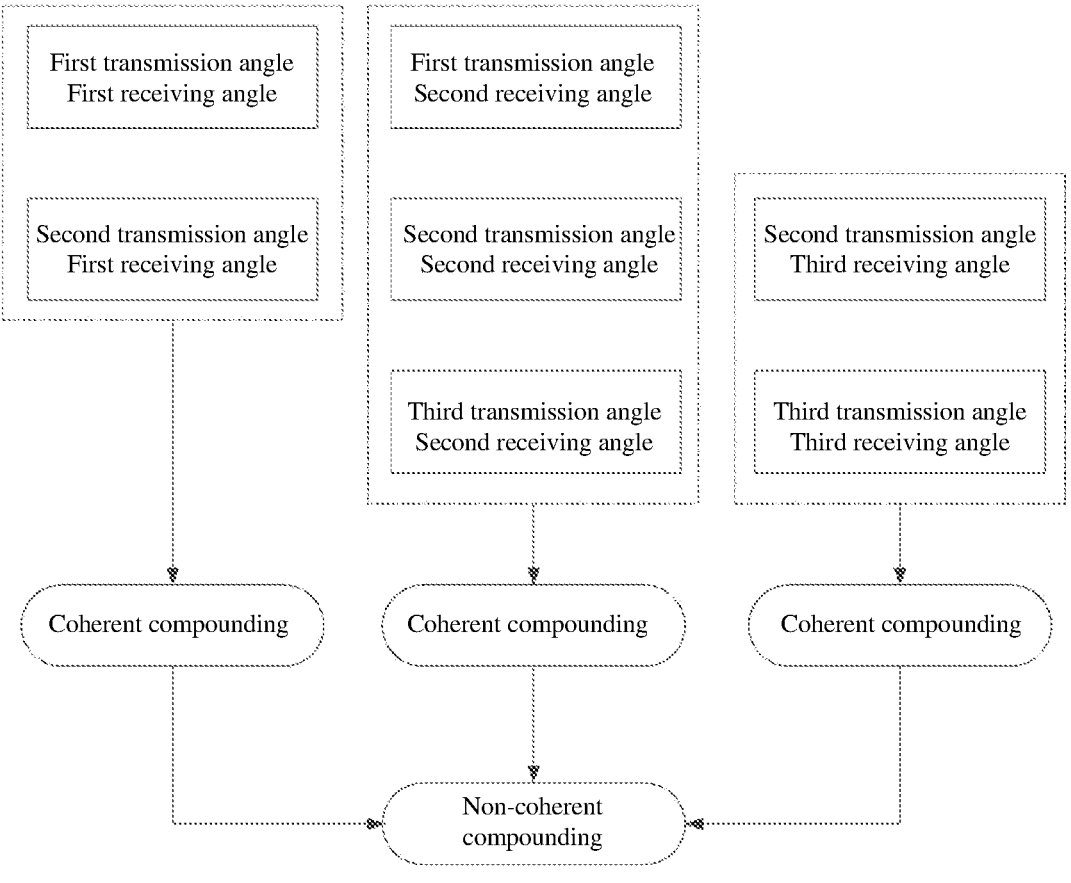
FIG. 5 is a schematic diagram of coherent compounding and non-coherent compounding according to an embodiment of the disclosure.

For example, in the example of FIG. 3, beamformed data of seven different transmission angles or different receiving angles are obtained in total. When performing coherent compounding and non-coherent compounding on the beamformed data obtained in FIG. 3, coherent compounding is first performed on the beamformed data corresponding to all the transmission angles for each receiving angle, and then non-coherent compounding is performed on the coherently compounded data corresponding to the three receiving angles. FIG. 5 is a schematic diagram of performing spatial compounding on the beamformed data obtained based on a transmitting and receiving strategy in FIG. 3. Coherent compounding is performed on beamformed data corresponding to the first transmission angle and the first receiving angle and beamformed data corresponding to the second transmission angle and the first receiving angle, to obtain first coherently compounded data corresponding to the first receiving angle; coherent compounding is performed on beamformed data corresponding to the first transmission angle and the second receiving angle, beamformed data corresponding to the second transmission angle and the second receiving angle, and beamformed data corresponding to the third transmission angle and the second receiving angle, to obtain second coherently compounded data corresponding to the second receiving angle; and coherent compounding is performed on beamformed data corresponding to the second transmission angle and the third receiving angle and beamformed data corresponding to the third transmission angle and the third receiving angle, to obtain third coherently compounded data corresponding to the third receiving angle. Then, non-coherent compounding is performed on the first coherently compounded data, the second coherently compounded data, and the third coherently compounded data to obtain the compounded data. The compounded data is used to form a frame of ultrasound image.

When coherent compounding or non-coherent compounding is performed, it is required to assign different weights to the beamformed data corresponding to the different angles, and for the different weights, different imaging effects may be achieved. In an embodiment, coherent compounding or non-coherent compounding may be performed based on a preset weight coefficient. The preset weight coefficient may be calculated based on a geometric positional relationship between a transmitted signal and a received signal of the ultrasound probe. Alternatively, when spatial compounding is performed, the weight coefficient may be calculated according to a set algorithm rule or adaptively calculated for coherent compounding or non-coherent compounding. An adaptive weight coefficient is a weight coefficient calculated based on characteristics of an ultrasound echo signal, and performing dynamic weighting based on the adaptive weight coefficient can effectively improve the image quality. Exemplarily, for coherent compounding, it may be required to calculate coherence between different beamformed data. A calculation method includes a coherence factor, an eigenvalue analysis, and the like, which can identify data with strong coherence and data with weak coherence, and a larger weight may be assigned to data with strong coherence. For non-coherent compounding, compounding methods used include average value compounding, taking a minimum value, taking a maximum value, adaptive calculation, and so on.

Then, in step S250, the ultrasound image is generated based on the compounded data. Specifically, image processing is performed on the compounded data to obtain displayable ultrasound image data, which is output to a display for display. Through coherent compounding and non-coherent compounding, both the hyperechoic and hypoechoic regions in the tissue can be well displayed, and a gray scale of the ultrasound image can be displayed clearly.

In conclusion, according to the ultrasound imaging method 200 in this embodiment of the disclosure, coherent compounding is performed on the beamformed data corresponding to the same receiving angle and different transmission angles, non-coherent compounding is performed on the coherently compounded data corresponding to different receiving angles, and amplitude information and phase information of data corresponding to different angles are combined, thereby improving the image quality of an ultrasound image.

Another aspect of an embodiment of the disclosure provides an ultrasound imaging method. Referring to FIG. 6, the ultrasound imaging method 600 includes the following steps.

In step S610, ultrasound waves are transmitted to a target tissue of a subject at at least two different transmission angles.

In step S620, an echo of the ultrasound wave is received at each transmission angle to obtain an ultrasound echo signal corresponding to each transmission angle.

In step S630, for the ultrasound echo signal corresponding to each transmission angle, beamforming is performed at at least two different receiving angles to obtain beamformed data corresponding to the different receiving angles.

In step S640, based on each transmission angle and the receiving angles corresponding to the beamformed data, at least one coherent compounding and at least one non-coherent compounding are performed on the beamformed data to obtain compounded data, where each coherent compounding includes performing coherent compounding on beamformed data corresponding to a same receiving angle and different transmission angles to obtain a set of coherently compounded data corresponding to the same receiving angle, and each non-coherent compounding includes performing non-coherent compounding on at least one set of coherently compounded data and the beamformed data not subjected to the coherent compounding.

In step S650, an ultrasound image is generated based on the compounded data.

Similar to the ultrasound imaging method 200 in the embodiment of the disclosure, the ultrasound imaging method 600 includes transmitting the ultrasound waves at the at least two transmission angles, and performing beamforming at the at least two receiving angles for the ultrasound echo signal corresponding to each transmission angle. The coherent compounding is performed on the beamformed data corresponding to the same receiving angle and the different transmission angles, and then the non-coherent compounding is performed on the coherently compounded data to obtain the compounded data, and the ultrasound image is generated based on the compounded data. A difference from the ultrasound imaging method 200 is that in the ultrasound imaging method 600 of this embodiment of the disclosure, the non-coherent compounding includes performing non-coherent compounding on coherently compounded data and beamformed data not subjected to the coherent compounding. The coherent compounding is performed on the beamformed data corresponding to the same receiving angle and the different transmission angles, and sound field information of different transmission angles may be compounded, which improves the image signal-to-noise ratio and spatial resolution, weakens the impact of a plurality of reflections at boundaries of strong echoes, and is beneficial to noise reduction in a lumen of a blood vessel. The non-coherent compounding is performed on the coherently compounded data and beamformed data not subjected to the coherent compounding, speckle noise may be suppressed, noise of an ultrasound image is reduced, and the image quality is further improved. Moreover, the coherent compounding of data at the same receiving angle may be performed based on the receiving aperture, which reduces the complexity of data processing.

Exemplarily, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles. In this way, each transmission angle may have a receiving angle parallel to the transmission angle and a deflected receiving angle thereof, and richer tissue information is provided while signal strength is ensured. When coherent compounding is performed, beamformed data corresponding to the at least two deflected transmission angles that are symmetrical to each other with respect to the vertical transmission angle may be extracted from beamformed data corresponding to the vertical receiving angle, and coherent compounding is performed on the beamformed data corresponding to the at least two deflected transmission angles, to obtain the coherently compounded data. When non-coherent compounding is performed, non-coherent compounding may be performed on at least one set of coherently compounded data that corresponds to the vertical receiving angle, and the beamformed data not subjected to the coherent compounding that corresponds to the vertical receiving angle and the vertical transmission angle. That is, because coherence between the beamformed data corresponding to the vertical receiving angle and the vertical transmission angle and beamformed data corresponding to another angle is relatively low, coherent compounding is not performed on the beamformed data corresponding to the vertical receiving angle and the vertical transmission angle.

Because a deflected receiving angle is further included in addition to the vertical receiving angle, the coherent compounding further includes performing coherent compounding on beamformed data corresponding to at least two different transmission angles corresponding to at least one of the deflected receiving angles to obtain coherently compounded data corresponding to the at least one deflected receiving angle. The data for the non-coherent compounding further includes the coherently compounded data corresponding to the at least one deflected receiving angle.

Figure 7:
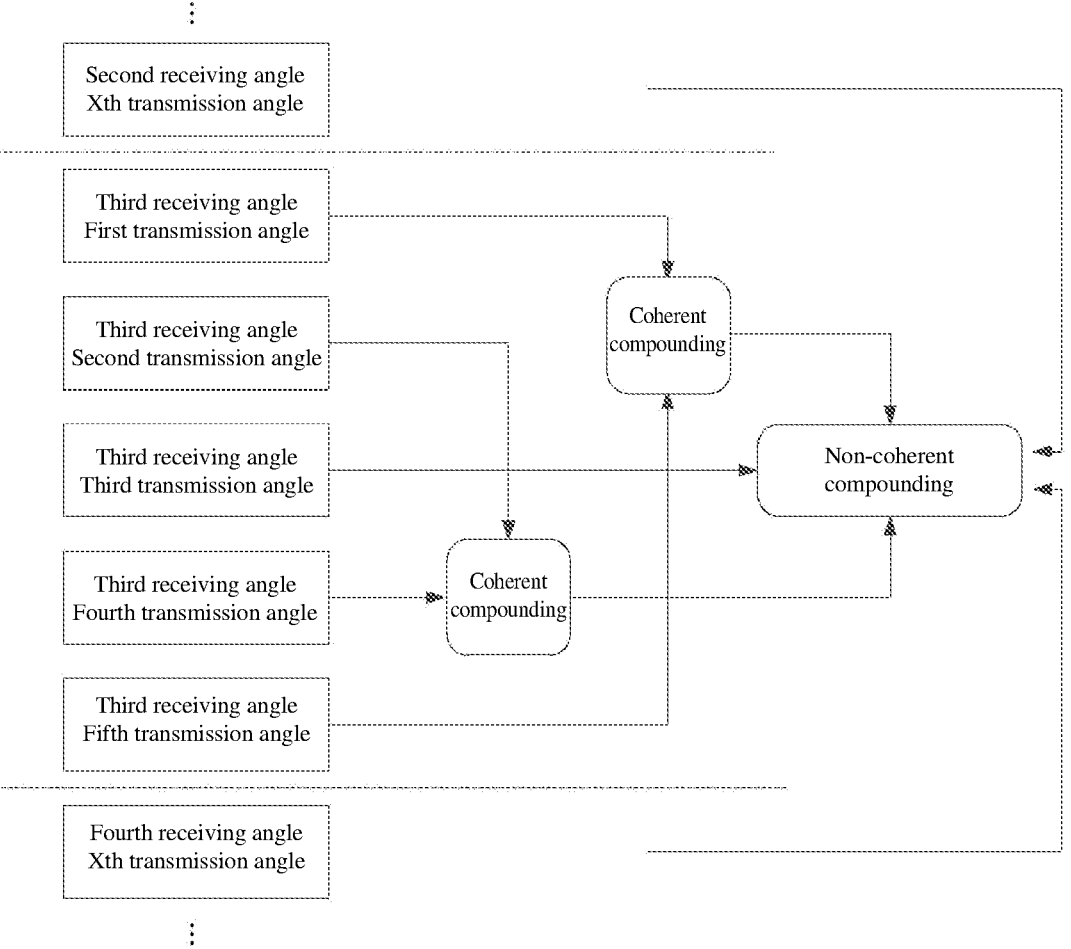
FIG. 7 is a schematic diagram of coherent compounding and non-coherent compounding according to another embodiment of the disclosure.

For example, referring to FIG. 7, the transmission angles include a first transmission angle, a second transmission angle, a third transmission angle, a fourth transmission angle, and a fifth transmission angle. The third transmission angle is the vertical transmission angle, the first transmission angle and the fifth transmission angle are the deflected transmission angles that are symmetrical to each other with respect to the third transmission angle, and the second transmission angle and the fourth transmission angle are the deflected transmission angles that are symmetrical to each other with respect to the third transmission angle; and receiving angles corresponding to the first transmission angle and the second transmission angle include a first receiving angle, a second receiving angle, and a third receiving angle, receiving angles corresponding to the third transmission angle include the first receiving angle, the second receiving angle, the third receiving angle, a fourth receiving angle, and a fifth receiving angle, receiving angles corresponding to the fourth transmission angle and the fifth transmission angle include the third receiving angle, a fourth receiving angle, and a fifth receiving angle, the third receiving angle is the vertical receiving angle, the first receiving angle and the fifth receiving angle are deflected receiving angles that are symmetrical to each other with respect to the third receiving angle, and the second receiving angle and the fourth receiving angle are deflected receiving angles that are symmetrical to each other with respect to the third receiving angle.

When coherent compounding is performed, coherent compounding may be performed on beamformed data corresponding to the third receiving angle and the first transmission angle and beamformed data corresponding to the third receiving angle and the fifth transmission angle, to obtain fourth coherently compounded data; coherent compounding is performed on beamformed data corresponding to the third receiving angle and the second transmission angle and beamformed data corresponding to the third receiving angle and the fourth transmission angle, to obtain fifth coherently compounded data; and the data for the non-coherent compounding includes the fourth coherently compounded data, the fifth coherently compounded data, and beamformed data corresponding to the third receiving angle and the third transmission angle. Certainly, the data for the non-coherent compounding further includes coherently compounded data corresponding to another receiving angle.

In conclusion, according to the ultrasound imaging method 600 in this embodiment of the disclosure, coherent compounding is performed on the beamformed data corresponding to the same receiving angle and different transmission angles, non-coherent compounding is performed on the coherently compounded data and beamformed data not subjected to the coherent compounding, and amplitude information and phase information of data corresponding to different angles are combined, thereby improving the image quality of an ultrasound image.

Another aspect of an embodiment of the disclosure provides an ultrasound imaging method. Referring to FIG. 8, the ultrasound imaging method 800 includes the following steps.

In step S810, ultrasound waves are transmitted to a target tissue of a subject at at least two different transmission angles.

In step S820, an echo of the ultrasound wave is received at each transmission angle to obtain an ultrasound echo signal corresponding to each transmission angle.

In step S830, for the ultrasound echo signal corresponding to each transmission angle, beamforming is performed at at least two different receiving angles to obtain beamformed data corresponding to the different receiving angles.

In step S840, based on each transmission angle and the receiving angles corresponding to the beamformed data, at least one coherent compounding and at least one non-coherent compounding are performed on the beamformed data to obtain compounded data, where each coherent compounding includes performing coherent compounding on beamformed data corresponding to a same transmission angle and different receiving angles to obtain a set of coherently compounded data corresponding to the same transmission angle, and each non-coherent compounding includes performing non-coherent compounding on at least two sets of coherently compounded data.

In step S850, an ultrasound image is generated based on the compounded data.

Similar to the ultrasound imaging method 200 in the embodiments of the disclosure, the ultrasound imaging method 800 also includes transmitting the ultrasound waves at the at least two transmission angles, and performing beamforming at the at least two receiving angles for the ultrasound echo signal corresponding to each transmission angle. A difference from the ultrasound imaging method 200 is that in the ultrasound imaging method 800 of this embodiment of the disclosure, the coherent compounding is performed on the beamformed data corresponding to the same transmission angle and the different receiving angles, and then the non-coherent compounding is performed on the coherently compounded data to obtain the compounded data, and the ultrasound image is generated based on the compounded data. The coherent compounding is performed on the beamformed data corresponding to the same transmission angle and the different receiving angles, and sound field information of different receiving angles may be compounded, which improves the image signal-to-noise ratio and spatial resolution, weakens the impact of a plurality of reflections at boundaries of strong echoes, and is beneficial to noise reduction in a lumen of a blood vessel. The non-coherent compounding is performed on the coherently compounded data corresponding to the different transmission angles, speckle noise may be suppressed, noise of an ultrasound image is reduced, and the image quality is further improved.

In some embodiments, coherent compounding is performed on the beamformed data corresponding to all receiving angles for each transmission angle, that is, performing coherent compounding on the beamformed data corresponding to all the receiving angles for each transmission angle to obtain coherently compounded data corresponding to each transmission angle. Then, non-coherent compounding is performed on the coherently compounded data corresponding to all transmission angles to obtain the compounded data. That is, the number of times of coherent compounding is same as the number of transmission angles, and then non-coherent compounding is uniformly performed on all coherently compounded data. The non-coherent compounding may be performed once or a plurality of times.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles respectively parallel to the at least two deflected transmission angles. Exemplarily, an included angle between a line along which each transmission angle is located and a line along which a corresponding receiving angle is located does not exceed a maximum included angle between a normal direction of an array element that transmits the ultrasound wave and the transmission angle, to ensure signal strength. A number of different receiving angles among all the receiving angles is same as that of different transmission angles among all the transmission angles, to reduce the difficulty of data processing.

Figure 9:
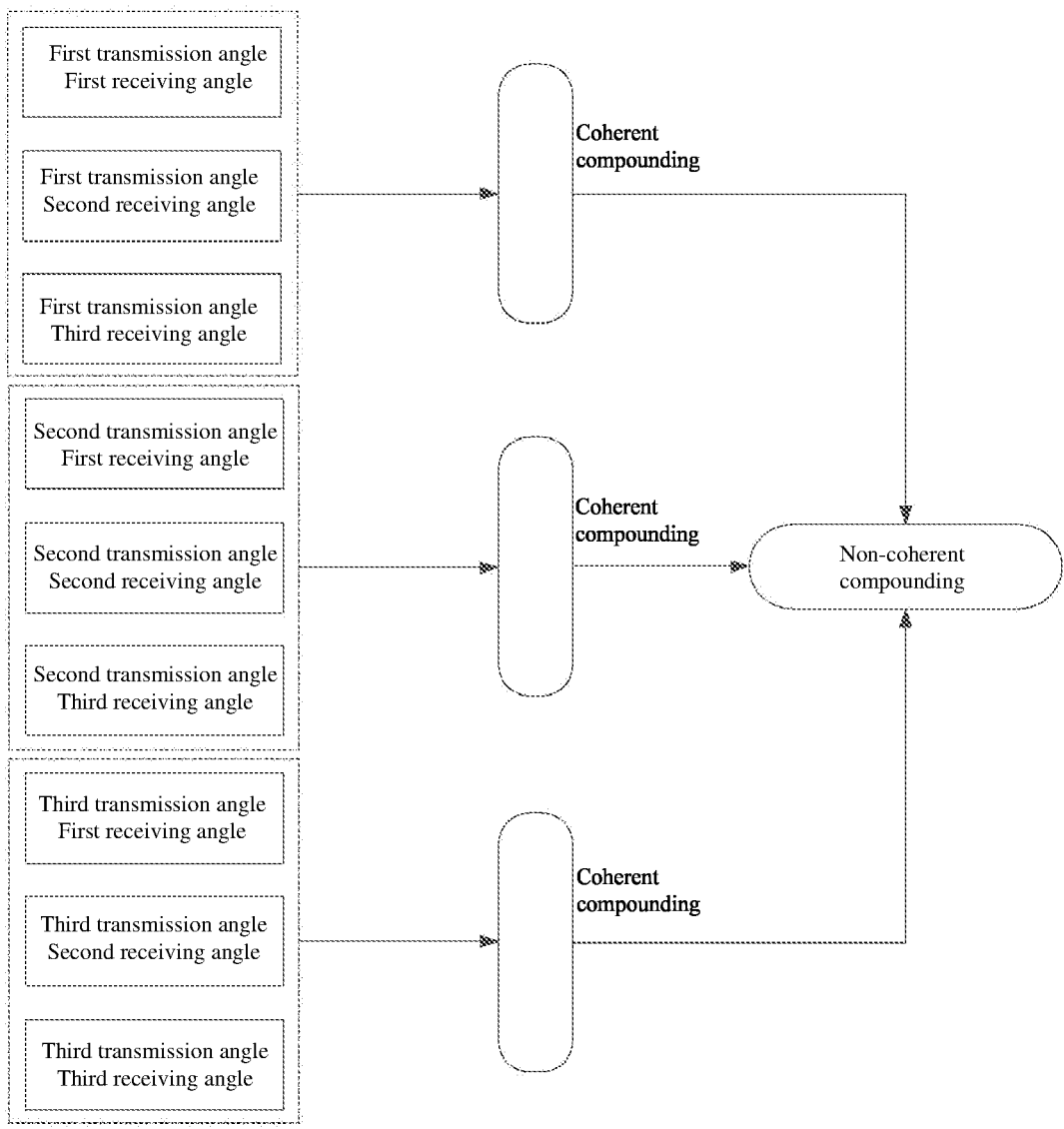
FIG. 9 is a schematic diagram of coherent compounding and non-coherent compounding according to another embodiment of the disclosure.

In an example, as shown in FIG. 9, the transmission angles include a first transmission angle, a second transmission angle, and a third transmission angle, the second transmission angle is the vertical transmission angle, and the first transmission angle and the third transmission angle are the deflected transmission angles that are symmetrical to each other with respect to the second transmission angle; and receiving angles corresponding to the first transmission angle include a first receiving angle and a second receiving angle, receiving angles corresponding to the second transmission angle include the first receiving angle, the second receiving angle, and a third receiving angle, receiving angles corresponding to the third transmission angle include the second receiving angle and the third receiving angle, the second receiving angle is the vertical receiving angle, and the first receiving angle and the third receiving angle are respectively parallel to the first transmission angle and the third transmission angle.

In this example, coherent compounding is performed on beamformed data corresponding to the first transmission angle and the first receiving angle and beamformed data corresponding to the first transmission angle and the second receiving angle, to obtain sixth coherently compounded data; coherent compounding is performed on beamformed data corresponding to the second transmission angle and the first receiving angle, beamformed data corresponding to the second transmission angle and the second receiving angle, and beamformed data corresponding to the second transmission angle and the third transmission angle, to obtain seventh coherently compounded data; and coherent compounding is performed on beamformed data corresponding to the third transmission angle and the second receiving angle and beamformed data corresponding to the third transmission angle and the third receiving angle, to obtain eighth coherently compounded data. After the sixth coherently compounded data, the seventh coherently compounded data, and the eighth coherently compounded data are obtained, non-coherent compounding is performed on the sixth coherently compounded data, the seventh coherently compounded data, and the eighth coherently compounded data to obtain the compounded data used to generate a frame of ultrasound image.

According to the ultrasound imaging method 800 in this embodiment of the disclosure, coherent compounding is performed on the beamformed data corresponding to the same transmission angle and different receiving angles, non-coherent compounding is performed on the coherently compounded data corresponding to different transmission angles, and amplitude information and phase information of data corresponding to different angles are combined, thereby improving the image quality of an ultrasound image. For more specific details of the ultrasound imaging method 800, reference may be made to the related description of the ultrasound imaging method 200. Details are not described herein again.

Another aspect of an embodiment of the disclosure provides an ultrasound imaging method. Referring to FIG. 10, the ultrasound imaging method 1000 includes the following steps.

In step S1010, ultrasound waves are transmitted to a target tissue of a subject at at least two different transmission angles.

In step S1020, an echo of the ultrasound wave is received at each transmission angle to obtain an ultrasound echo signal corresponding to each transmission angle.

In step S1030, for the ultrasound echo signal corresponding to each transmission angle, beamforming is performed at at least two different receiving angles to obtain beamformed data corresponding to the different receiving angles.

In step S1040, based on each transmission angle and the receiving angles corresponding to the beamformed data, at least one coherent compounding and at least one non-coherent compounding are performed on the beamformed data to obtain compounded data, where each coherent compounding includes performing coherent compounding on beamformed data corresponding to a same transmission angle and different receiving angles to obtain a set of coherently compounded data, and each non-coherent compounding includes performing non-coherent compounding on at least one set of coherently compounded data and the beamformed data not subjected to the coherent compounding.

In step S1050, an ultrasound image is generated based on the compounded data.

Similar to the ultrasound imaging method 800 in the embodiments of the disclosure, the ultrasound imaging method 1000 also includes transmitting the ultrasound waves at the at least two transmission angles, and performing beamforming at the at least two receiving angles for the ultrasound echo signal corresponding to each transmission angle. A difference from the ultrasound imaging method 800 is that in the ultrasound imaging method 1000 of this embodiment of the disclosure, the coherent compounding is performed on the beamformed data corresponding to the same transmission angle and the different receiving angles, and then the non-coherent compounding is performed on the coherently compounded data and the beamformed data not subjected to the coherent compounding, to obtain the compounded data, and the ultrasound image is generated based on the compounded data. The coherent compounding is performed on the beamformed data corresponding to the same transmission angle and the different receiving angles, and sound field information of different receiving angles may be compounded, which improves the image signal-to-noise ratio and spatial resolution, weakens the impact of a plurality of reflections at boundaries of strong echoes, and is beneficial to noise reduction in a lumen of a blood vessel. The non-coherent compounding is performed on the coherently compounded data and beamformed data not subjected to the coherent compounding, speckle noise may be suppressed, noise of an ultrasound image is reduced, and the image quality is further improved.

In some embodiments, the transmission angles include a vertical transmission angle perpendicular to a plane where an array element that transmits the ultrasound wave is located and at least two deflected transmission angles that are symmetrical to each other with respect to the vertical transmission angle; and the receiving angles include a vertical receiving angle parallel to the vertical transmission angle and at least two deflected receiving angles parallel to the at least two deflected transmission angles.

In some embodiments, beamformed data corresponding to the at least two deflected receiving angles that are symmetrical to each other with respect to the vertical receiving angle may be extracted from beamformed data corresponding to the vertical transmission angle, and coherent compounding is performed on the beamformed data corresponding to the at least two deflected receiving angles, to obtain the coherently compounded data, so as to improve the data coherence. Data for the non-coherent compounding includes at least one set of coherently compounded data that corresponds to the vertical transmission angle, and the beamformed data not subjected to the coherent compounding that corresponds to the vertical transmission angle and the vertical receiving angle. That is, because coherence between the beamformed data corresponding to the vertical receiving angle and the vertical transmission angle and beamformed data corresponding to another angle is relatively low, coherent compounding is not performed on the beamformed data corresponding to the vertical receiving angle and the vertical transmission angle.

Because the transmission angle further includes a deflected transmission angle, performing coherent compounding on beamformed data corresponding to the same transmission angle and different receiving angles to obtain coherently compounded data further includes: performing coherent compounding on beamformed data corresponding to at least two different receiving angles corresponding to at least one of the deflected transmission angles to obtain coherently compounded data corresponding to the at least one deflected transmission angle; and the data for the non-coherent compounding further includes the coherently compounded data corresponding to the at least one deflected transmission angle.

Figure 11:
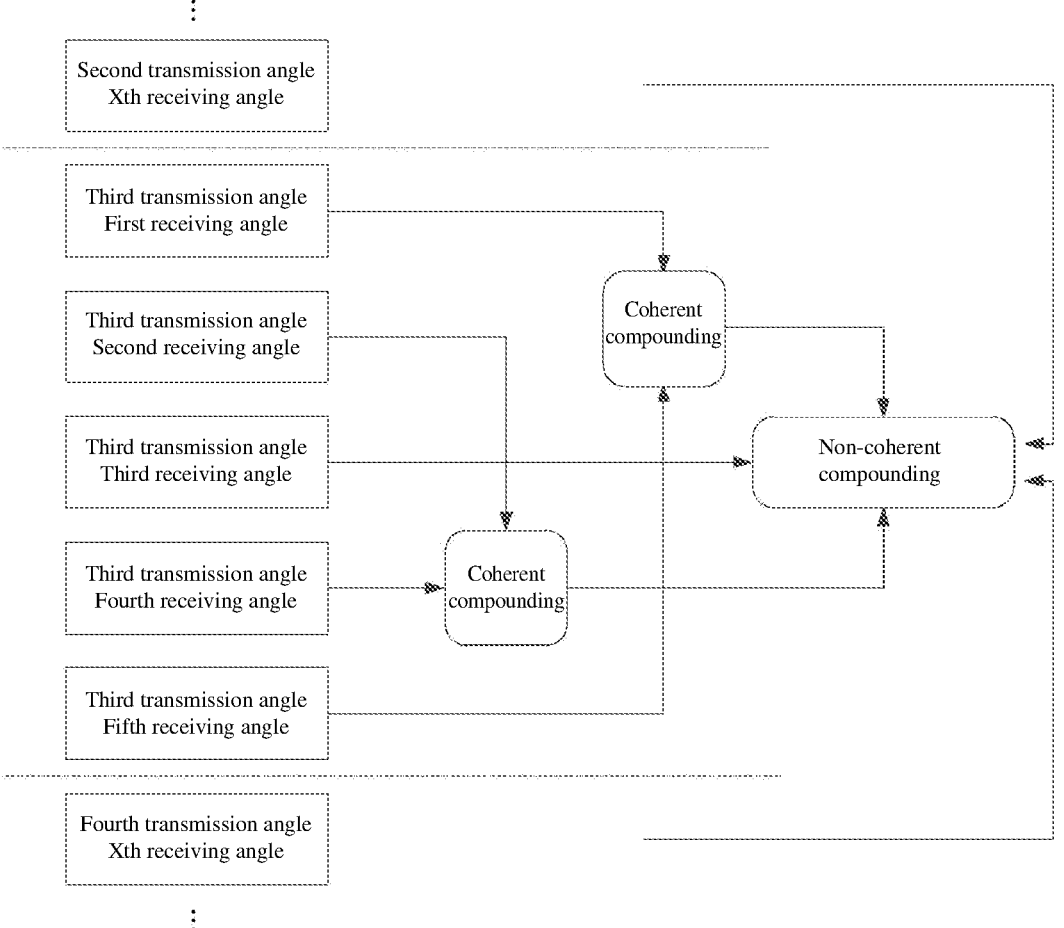
FIG. 11 is a schematic diagram of coherent compounding and non-coherent compounding according to another embodiment of the disclosure.

In an example, as shown in FIG. 11, the transmission angles include a first transmission angle, a second transmission angle, a third transmission angle, a fourth transmission angle, and a fifth transmission angle, the third transmission angle is the vertical transmission angle, the first transmission angle and the fifth transmission angle are the deflected transmission angles that are symmetrical to each other with respect to the third transmission angle, and the second transmission angle and the fourth transmission angle are the deflected transmission angles that are symmetrical to each other with respect to the third transmission angle; and receiving angles corresponding to the first transmission angle and the second transmission angle include a first receiving angle, a second receiving angle, and a third receiving angle, receiving angles corresponding to the third transmission angle include the first receiving angle, the second receiving angle, the third receiving angle, a fourth receiving angle, and a fifth receiving angle, receiving angles corresponding to the fourth transmission angle and the fifth transmission angle include the third receiving angle, the fourth receiving angle, and the fifth receiving angle, the third receiving angle is the vertical receiving angle, the first receiving angle and the fifth receiving angle are deflected receiving angles that are symmetrical to each other with respect to the third receiving angle, and the second receiving angle and the fourth receiving angle are deflected receiving angles that are symmetrical to each other with respect to the third receiving angle.

When transmission and receiving are performed based on the above transmitting and receiving strategy, coherent compounding may be performed on beamformed data corresponding to the third transmission angle and the first receiving angle and beamformed data corresponding to the third transmission angle and the fifth receiving angle, to obtain ninth coherently compounded data; and coherent compounding may be performed on beamformed data corresponding to the third transmission angle and the second receiving angle and beamformed data corresponding to the third transmission angle and the fourth receiving angle, to obtain tenth coherently compounded data. The data for the non-coherent compounding includes the ninth coherently compounded data, the tenth coherently compounded data, and beamformed data corresponding to the third transmission angle and the third receiving angle. In addition, the data for the non-coherent compounding may further include coherently compounded data at other transmission angles.

In conclusion, according to the ultrasound imaging method 1000 in this embodiment of the disclosure, coherent compounding is performed on the beamformed data corresponding to the same transmission angle and different receiving angles, non-coherent compounding is performed on the coherently compounded data and beamformed data not subjected to the coherent compounding, and amplitude information and phase information of data corresponding to different angles are combined, thereby improving the image quality of an ultrasound image.

An embodiment of the disclosure further provides an ultrasound imaging system, which is configured to implement the above ultrasound imaging method 200, ultrasound imaging method 600, ultrasound imaging method 800, or ultrasound imaging method 1000. Referring now to FIG. 1 again, the ultrasound imaging system may be implemented as the ultrasound imaging system 100 shown in FIG. 1. The ultrasound imaging system 100 may include an ultrasound probe 110, a transmitter circuit 112, a receiver circuit 114, a processor 116, and a display 118. Optionally, the ultrasound imaging system 100 may further include a transmitting/receiving selection switch 120 and a beamforming module 122, and the transmitter circuit 112 and the receiver circuit 114 may be connected to the ultrasound probe 110 through the transmitting/receiving selection switch 120. For the related description of the components, reference may be made to the related description above. Details are not described herein again.

The transmitter circuit 112 is configured to excite the ultrasound probe 110 to transmit an ultrasound wave to a target tissue. The receiver circuit 114 is configured to control the ultrasound probe 110 to receive an echo of the ultrasound wave, to obtain an ultrasound echo signal. The processor 116 is configured to perform the steps of the above ultrasound imaging method 200, ultrasound imaging method 600, ultrasound imaging method 800, or ultrasound imaging method 1000. The processor 116 is further configured to control the display 118 to display an ultrasound image.

The above describes only the main functions of the components of the ultrasound imaging system, and for more details, reference may be made to the related description of the ultrasound imaging method. According to the ultrasound imaging system in the embodiments of the disclosure, both coherent compounding and non-coherent compounding are performed on beamformed data corresponding to different transmission angles or different receiving angles, and amplitude information and phase information of data corresponding to different angles are combined, thereby improving the image quality of an ultrasound image.

While example embodiments have been described herein with reference to the accompanying drawings, it should be understood that the above example embodiments are merely illustrative and are not intended to limit the scope of the disclosure thereto. Those of ordinary skill in the art may make various changes and modifications therein without departing from the scope and spirit of the disclosure. All such changes and modifications are intended to be included in the scope of the disclosure as claimed in the appended claims.

Those of ordinary skill in the art would have appreciated that the units and algorithm steps of the examples described in conjunction with the embodiments disclosed herein may be implemented in electronic hardware or a combination of computer software and electronic hardware. Whether the functions are performed by hardware or software depends on particular applications and design constraint conditions of the technical solutions. Those skilled in the art could use different methods to implement the described functions for each particular application, but such implementation should not be considered to be beyond the scope of the disclosure.

In several embodiments provided in the present disclosure, it is to be understood that the disclosed devices and methods may be implemented in other ways. For example, the device embodiments described above are merely exemplary. For example, the division of units is merely a logical function division. In actual implementations, there may be other division methods. For example, a plurality of units or assemblies may be combined or integrated into another device, or some features may be omitted or not implemented.

A large number of specific details are explained in this description provided herein. However, it can be understood that the embodiments of the disclosure can be practiced without these specific details. In some instances, well-known methods, structures, and technologies are not shown in detail, so as not to obscure the understanding of this description.

Similarly, it should be understood that in order to simplify the disclosure and help to understand one or more of various aspects of the disclosure, in the description of the exemplary embodiments of the disclosure, various features of the disclosure are sometimes together grouped into an individual embodiment, figure or description thereof. However, the method of the disclosure should not be construed as reflecting the following intention: namely, the disclosure set forth requires more features than those explicitly stated in each claim. More precisely, as reflected by the corresponding claims, the inventive point thereof lies in that features that are fewer than all the features of an individual embodiment disclosed may be used to solve the corresponding technical problem. Therefore, the claims in accordance with the particular embodiments are thereby explicitly incorporated into the particular embodiments, where each claim itself serves as an individual embodiment of the disclosure.

Those skilled in the art should understand that, in addition to the case where features are mutually exclusive, any combination may be used to combine all the features disclosed in this description (along with the appended claims, abstract, and drawings) and all the processes or units of any of methods or apparatuses as disclosed. Unless explicitly stated otherwise, each feature disclosed in this description (along with the appended claims, abstract, and drawings) may be replaced by an alternative feature that provides the same, equivalent, or similar objective.

Furthermore, those skilled in the art should understand that although some of the embodiments described herein include some but not other features included in other embodiments, combinations of features of different embodiments are meant to be within the scope of the disclosure, and form different embodiments. For example, in the claims, any one of the embodiments set forth thereby may be used in any combination.

Various embodiments regarding components in the disclosure may be implemented in hardware, or implemented by software modules running on one or more processors, or implemented in a combination thereof. It should be understood for those skilled in the art that a microprocessor or a digital signal processor (DSP) may be used in practice to implement some or all of the functions of some modules according to the embodiments of the disclosure. The disclosure may further be implemented as an apparatus program (e.g. a computer program and a computer program product) for executing some or all of the methods described herein. Such a program for implementing the disclosure may be stored on a computer-readable medium, or may be in the form of one or more signals. Such a signal may be downloaded from an Internet website, or provided on a carrier signal, or provided in any other form.

It should be noted that the description of the disclosure made in the above-mentioned embodiments is not to limit the disclosure, and those skilled in the art may design alternative embodiments without departing from the scope of the appended claims. In the claims, any reference signs placed between parentheses should not be construed as limitation on the claims. The disclosure may be implemented by means of hardware including several different elements and by means of an appropriately programmed computer. In unit claims listing several apparatuses, several of these apparatuses may be specifically embodied by one and the same item of hardware. The use of the terms "first", "second", "third", etc. does not indicate any order. These terms may be interpreted as names.

The above descriptions are merely the specific embodiments of the disclosure or the description of the specific embodiments, but the scope of protection of the disclosure is not limited thereto. Changes or substitutions which may be readily contemplated by those skilled in the art within the technical scope disclosed in the disclosure fall within the scope of protection of the disclosure. The scope of protection of the disclosure should be subject to the scope of protection of the claims.

What is claimed is:

1. An ultrasound imaging method, comprising:
transmitting ultrasound waves to a target tissue of a subject at at least two transmission angles different from each other, respectively;
for the ultrasound wave transmitted at each transmission angle of at least two transmission angles, receiving an echo of the ultrasound wave returned by the target tissue to obtain an ultrasound echo signal corresponding to the transmission angle;
performing beamforming on the ultrasound echo signal corresponding to each transmission angle at at least two receiving angles different from each other, to obtain sets of beamformed data corresponding to the at least two receiving angles and the at least two transmission angles, wherein each of the sets of beamforming data corresponds to each of the at least two receiving angles for each transmitting angle;

performing at least two coherent compounding on the sets of beamformed data to obtain at least two sets of coherently compounded data, wherein performing each of the at least two coherent compounding comprises: for each receiving angle of the at least two receiving angles, performing coherent compounding on at least two of the sets of beamformed data corresponding to the receiving angle and different ones of the at least two transmission angles to obtain one of the at least two sets of coherently compounded data corresponding to the receiving angle;

performing non-coherent compounding on two or more of the at least two sets of coherently compounded data to obtain compounded data; and generating an ultrasound image based on the compounded data.

2. The ultrasound imaging method of claim 1, wherein for each receiving angle, performing the coherent compounding on the at least two of the sets of beamformed data corresponding to the receiving angle and the different ones of the at least two transmission angles to obtain one of the at least two sets of coherently compounded data corresponding to the receiving angle comprises:

performing coherent compounding on a portion of the sets of the beamformed data corresponding to all of the at least two transmission angles for each receiving angle to obtain coherently compounded data corresponding to the receiving angle; and performing the non-coherent compounding on the two or more of the at least two sets of coherently compounded data comprises: performing non-coherent compounding on the coherently compounded data corresponding to all of the at least two receiving angles to obtain the compounded data.

3. The ultrasound imaging method of claim 1, wherein the transmission angles comprise a vertical transmission angle perpendicular to a plane where an array element that transmits the ultrasound wave is located and at least two deflected transmission angles that are symmetrical to each other with respect to the vertical transmission angle; and the receiving angles comprise a vertical receiving angle parallel to the vertical transmission angle and at least two deflected receiving angles respectively parallel to the at least two deflected transmission angles.

4. The ultrasound imaging method of claim 3, wherein the transmission angles comprise a first transmission angle, a second transmission angle, and a third transmission angle, the second transmission angle is the vertical transmission angle, and the first transmission angle and the third transmission angle are the deflected transmission angles that are symmetrical to each other with respect to the second transmission angle;

ones of the receiving angles corresponding to the first transmission angle comprise a first receiving angle and a second receiving angle, ones of the receiving angles corresponding to the second transmission angle comprise the first receiving angle, the second receiving angle, and a third receiving angle, ones of the receiving angles corresponding to the third transmission angle comprise the second receiving angle and the third receiving angle, the second receiving angle is the vertical receiving angle, and the first receiving angle and the third receiving angle are respectively parallel to the first transmission angle and the third transmission angle;

performing the at least two coherent compounding on the sets of beamformed data to obtain the at least two sets of coherently compounded data comprises:

performing coherent compounding on one of the sets of beamformed data corresponding to the first transmission angle and the first receiving angle and one of the sets of beamformed data corresponding to the second transmission angle and the first receiving angle, to obtain first coherently compounded data;

performing coherent compounding on one of the sets of beamformed data corresponding to the first transmission angle and the second receiving angle, one of the sets of beamformed data corresponding to the second transmission angle and the second receiving angle, and one of the sets of beamformed data corresponding to the third transmission angle and the second receiving angle, to obtain second coherently compounded data; and performing coherent compounding on one of the sets of beamformed data corresponding to the second transmission angle and the third receiving angle and one of the sets of beamformed data corresponding to the third transmission angle and the third receiving angle, to obtain third coherently compounded data; and performing the non-coherent compounding on the two or more of the at least two sets of coherently compounded data to obtain the compounded data comprises: performing non-coherent compounding on the first coherently compounded data, the second coherently compounded data, and the third coherently compounded data to obtain the compounded data.

5. The ultrasound imaging method of claim 1, wherein an included angle between a line along which each transmission angle is located and a line along which a corresponding one of the at least two receiving angles is located does not exceed a maximum included angle between a normal direction of an array element that transmits the ultrasound wave and the transmission angle.

6. The ultrasound imaging method of claim 1, wherein a number of different receiving angles among all receiving angles is same as that of different transmission angles among all transmission angles.

7. The ultrasound imaging method of claim 3, wherein the transmission angles comprise a first transmission angle, a second transmission angle, a third transmission angle, a fourth transmission angle, and a fifth transmission angle, the third transmission angle is the vertical transmission angle, the first transmission angle and the fifth transmission angle are the deflected transmission angles that are symmetrical to each other with respect to the third transmission angle, and the second transmission angle and the fourth transmission angle are the deflected transmission angles that are symmetrical to each other with respect to the third transmission angle;

ones of the receiving angles corresponding to the first transmission angle and the second transmission angle comprise a first receiving angle, a second receiving angle, and a third receiving angle, ones of the receiving angles corresponding to the third transmission angle comprise the first receiving angle, the second receiving angle, the third receiving angle, a fourth receiving angle, and a fifth receiving angle, ones of the receiving angles corresponding to the fourth transmission angle and the fifth transmission angle comprise the third receiving angle, the fourth receiving angle, and the fifth receiving angle, the third receiving angle is the vertical receiving angle, the first receiving angle and the fifth receiving angle are the deflected receiving angles that are symmetrical to each other with respect to the third receiving angle, and the second receiving angle and the fourth receiving angle are the deflected receiving angles that are symmetrical to each other with respect to the third receiving angle;

performing the at least two coherent compounding on the sets of beamformed data to obtain the at least two sets of coherently compounded data comprises:

performing coherent compounding on one of the sets of beamformed data corresponding to the third receiving angle and the first transmission angle and one of the sets of beamformed data corresponding to the third receiving angle and the fifth transmission angle, to obtain fourth coherently compounded data; and performing coherent compounding on one of the sets of beamformed data corresponding to the third receiving angle and the second transmission angle and one of the sets of beamformed data corresponding to the third receiving angle and the fourth transmission angle, to obtain fifth coherently compounded data; and performing the non-coherent compounding on the two or more of the at least two sets of coherently compounded data to obtain the compounded data comprises: performing non-coherent compounding on the fourth coherently compounded data, the fifth coherently compounded data, and one of the sets of beamformed data corresponding to the third receiving angle and the third transmission angle, to obtain the compounded data.

* * * * *